US012064295B2

(12) United States Patent
Watson et al.

(10) Patent No.: US 12,064,295 B2
(45) Date of Patent: Aug. 20, 2024

(54) LIGHT HEAD HAVING CAMERA ASSEMBLY INTEGRATED IN HANDLE AND SURGICAL LIGHTING SYSTEM INCLUDING SAME

(71) Applicant: American Sterilizer Company, Mentor, OH (US)

(72) Inventors: Breese J. Watson, Rocky River, OH (US); Gregory Turcovsky, Mentor, OH (US); Steven H. Rus, Chardon, OH (US)

(73) Assignee: American Sterilizer Company, Mentor, OH (US)

( * ) Notice: Subject to any disclaimer, the term of this patent is extended or adjusted under 35 U.S.C. 154(b) by 434 days.

(21) Appl. No.: 17/212,240

(22) Filed: Mar. 25, 2021

(65) Prior Publication Data

US 2021/0298864 A1  Sep. 30, 2021

Related U.S. Application Data

(60) Provisional application No. 63/000,655, filed on Mar. 27, 2020, provisional application No. 63/000,672, (Continued)

(51) Int. Cl.
*A61B 90/30* (2016.01)
*A61B 90/00* (2016.01)
(Continued)

(52) U.S. Cl.
CPC ............ *A61B 90/30* (2016.02); *A61B 90/361* (2016.02); *A61B 90/37* (2016.02);
(Continued)

(58) Field of Classification Search
CPC . A61B 90/361; A61B 90/37; A61B 2090/306; A61B 2090/3614; G03B 15/14; G03B 17/561; G03B 30/00
(Continued)

(56) References Cited

U.S. PATENT DOCUMENTS 5,037,175 A    8/1991 Weber
5,515,472 A    5/1996 Mullaney et al.
(Continued)

FOREIGN PATENT DOCUMENTS

CN    102266248 A    12/2011

OTHER PUBLICATIONS

Steris; Surgical Solutions; A New Point of View; FREE5 Camera System Product Brochure; Apr. 2017.
(Continued)

*Primary Examiner* — Christopher E Mahoney
(74) *Attorney, Agent, or Firm* — Renner, Otto, Boisselle & Sklar, LLP

(57) ABSTRACT

A surgical lighting system includes a light head housing, a handle, a camera, and an optical fiber cable. The light head housing includes a plurality of light emitting elements therein that are arranged to emit light downward to a region of interest. The handle is mounted to the light head housing and protrudes downward from the light head housing, the handle including a handle housing having a sufficient size to be gripped by the human hand. A camera is mounted within the handle housing, the camera having a field of view that encompasses at least a portion of the region of interest. An optical fiber cable extends from a location within the handle housing and to the light head housing, the optical fiber cable being configured to transmit optical video signals associated with video data captured by the camera to the light head housing.

28 Claims, 24 Drawing Sheets

Related U.S. Application Data filed on Mar. 27, 2020, provisional application No. 63/000,719, filed on Mar. 27, 2020.

(51) Int. Cl.

| | | |
|---|---|---|
| *F21V 33/00* | (2006.01) | |
| *G02B 6/38* | (2006.01) | |
| *G03B 15/14* | (2021.01) | |
| *G03B 17/56* | (2021.01) | |
| *G03B 30/00* | (2021.01) | |
| *A61B 90/35* | (2016.01) | |
| *A61B 90/50* | (2016.01) | |
| *F21W 131/205* | (2006.01) | |

(52) U.S. Cl.
CPC ........ *F21V 33/0052* (2013.01); *G02B 6/3885* (2013.01); *G03B 15/14* (2013.01); *G03B 17/561* (2013.01); *G03B 30/00* (2021.01); *A61B 2090/306* (2016.02); *A61B 2090/308* (2016.02); *A61B 90/35* (2016.02); *A61B 2090/5025* (2016.02); *F21W 2131/205* (2013.01)

(58) Field of Classification Search
USPC ............................................ 600/249; 348/68
See application file for complete search history.

(56) References Cited

U.S. PATENT DOCUMENTS

| | | | |
|---|---|---|---|
| 5,590,234 A | 12/1996 | Pulido | |
| 5,617,501 A | 4/1997 | Miller et al. | |
| 6,014,490 A | 1/2000 | Canning et al. | |
| 6,134,370 A | 10/2000 | Childers et al. | |
| 6,464,383 B1 | 10/2002 | Northington et al. | |
| 6,507,691 B1 | 1/2003 | Hunsinger et al. | |
| 6,513,962 B1 | 2/2003 | Mayshack et al. | |
| 6,554,489 B2 | 4/2003 | Kent et al. | |
| 6,633,328 B1 | 10/2003 | Byrd | |
| 6,795,633 B2 | 9/2004 | Joseph, II | |
| 7,270,487 B2 | 9/2007 | Billman et al. | |
| 7,412,145 B2 | 8/2008 | Honma et al. | |
| 7,556,438 B2 | 7/2009 | Oike et al. | |
| 8,721,195 B2 * | 5/2014 | Doric | G02B 6/4298 385/88 |
| 8,774,585 B2 | 7/2014 | Kowalczyk et al. | |
| 9,726,829 B2 | 8/2017 | Benner et al. | |
| D887,624 S | 6/2020 | Debelak et al. | |
| D894,468 S | 8/2020 | Hollopeter et al. | |
| 2002/0012504 A1 | 1/2002 | Gillham et al. | |
| 2004/0120656 A1 | 6/2004 | Banas et al. | |
| 2005/0207711 A1 | 9/2005 | Vo et al. | |
| 2009/0122536 A1 | 5/2009 | Scholz | |
| 2013/0113945 A1 | 5/2013 | Tockweiler | |
| 2014/0193149 A1* | 7/2014 | Jones | H04B 10/80 398/43 |
| 2016/0091117 A1* | 3/2016 | Boccoleri | F16M 11/10 348/804 |
| 2019/0209261 A1 | 7/2019 | Hollopeter et al. | |

OTHER PUBLICATIONS

Getinge; Maquet Volista Surgical Light Product Brochure; Sep. 1, 2018.
Steris; Free5 Camera System Product Brochure; Nov. 1, 2011.
Steris; High Definition Camera Module Product Brochure; Dec. 2013.
Stryker; StrykeCam HD Product Brochure; Aug. 2018.
International Search Report and Written Opinion of the International Searching Authority for corresponding PCT International Application No. PCT/US2012/024106 mailed Oct. 12, 2021.
Invitation to Pay Additional Fees/Partial International Search for corresponding PCT International Application No. PCT/ US2012/ 0241106 mailed Jul. 15, 2021.

* cited by examiner

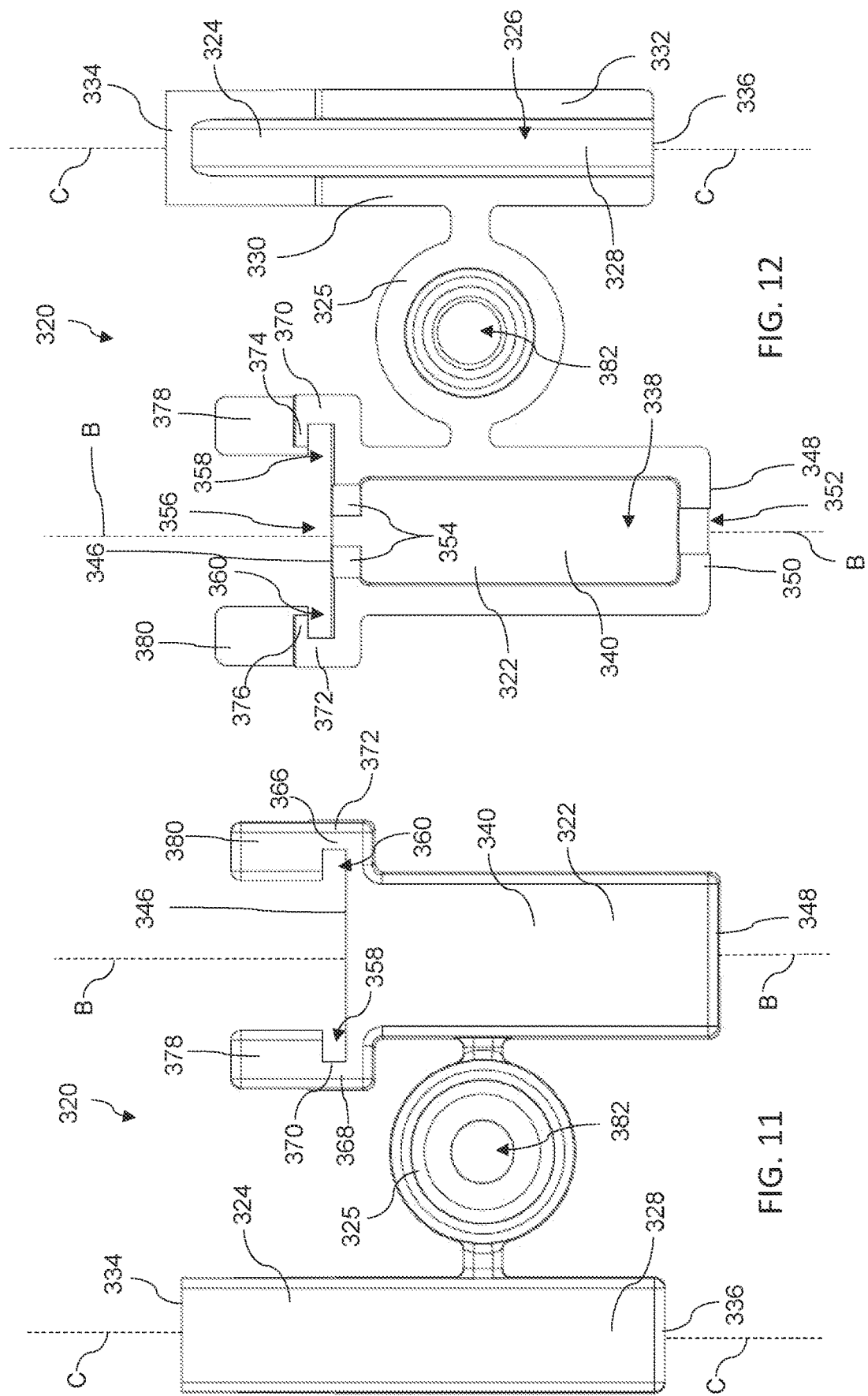

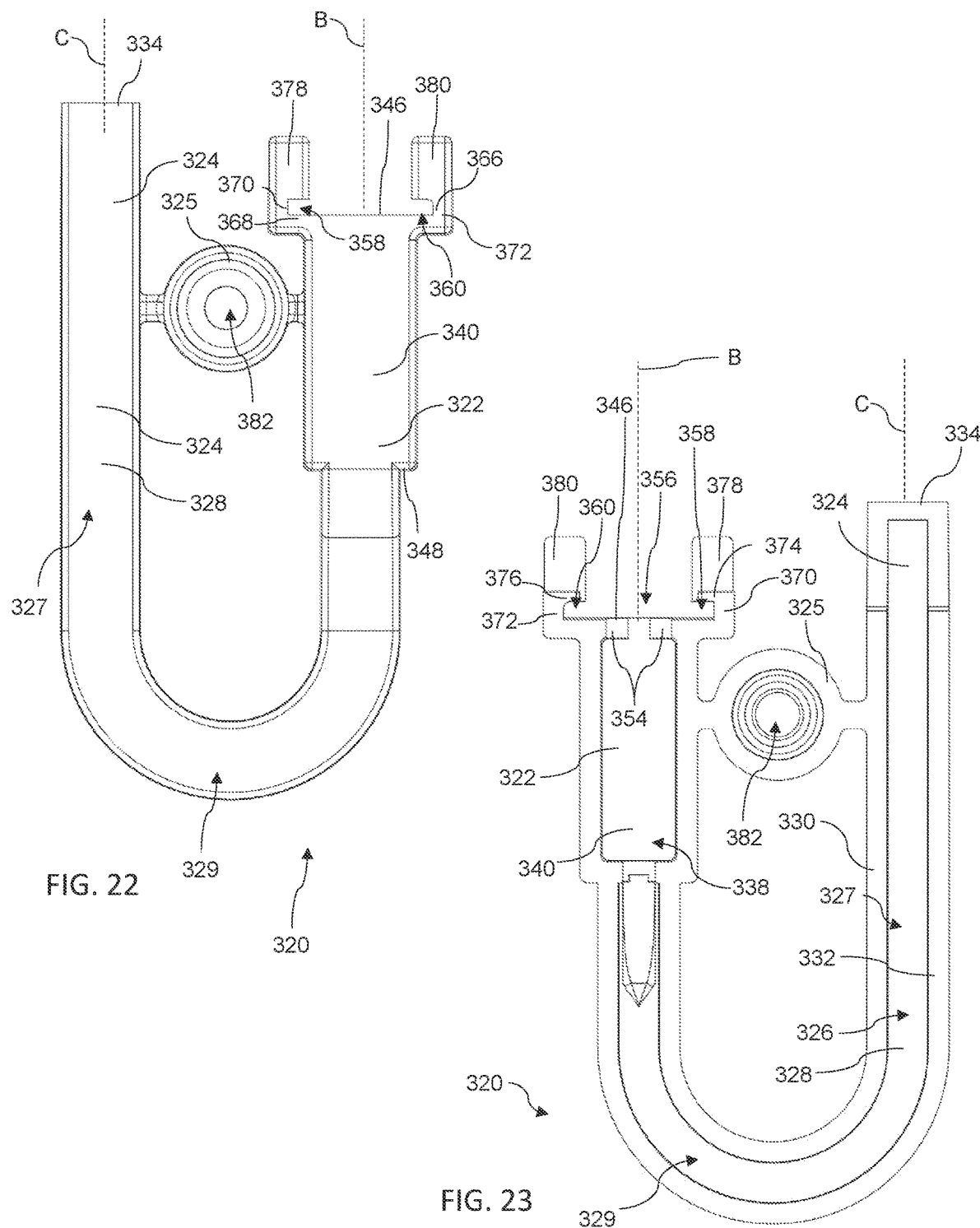

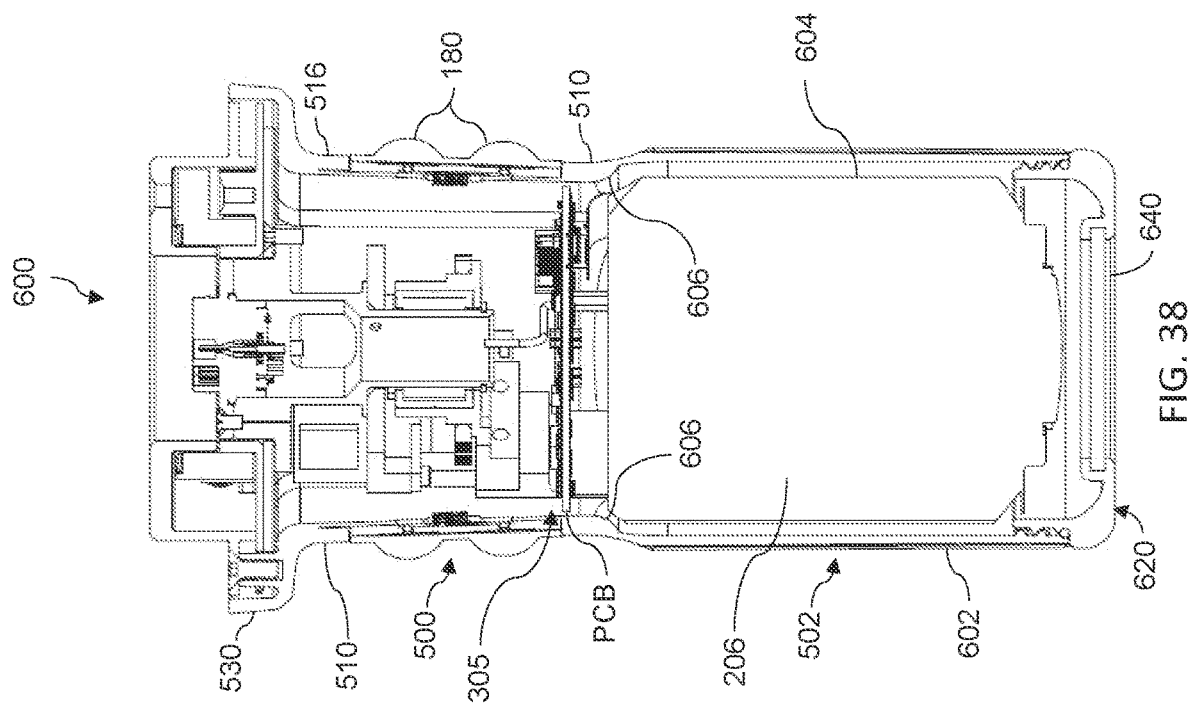
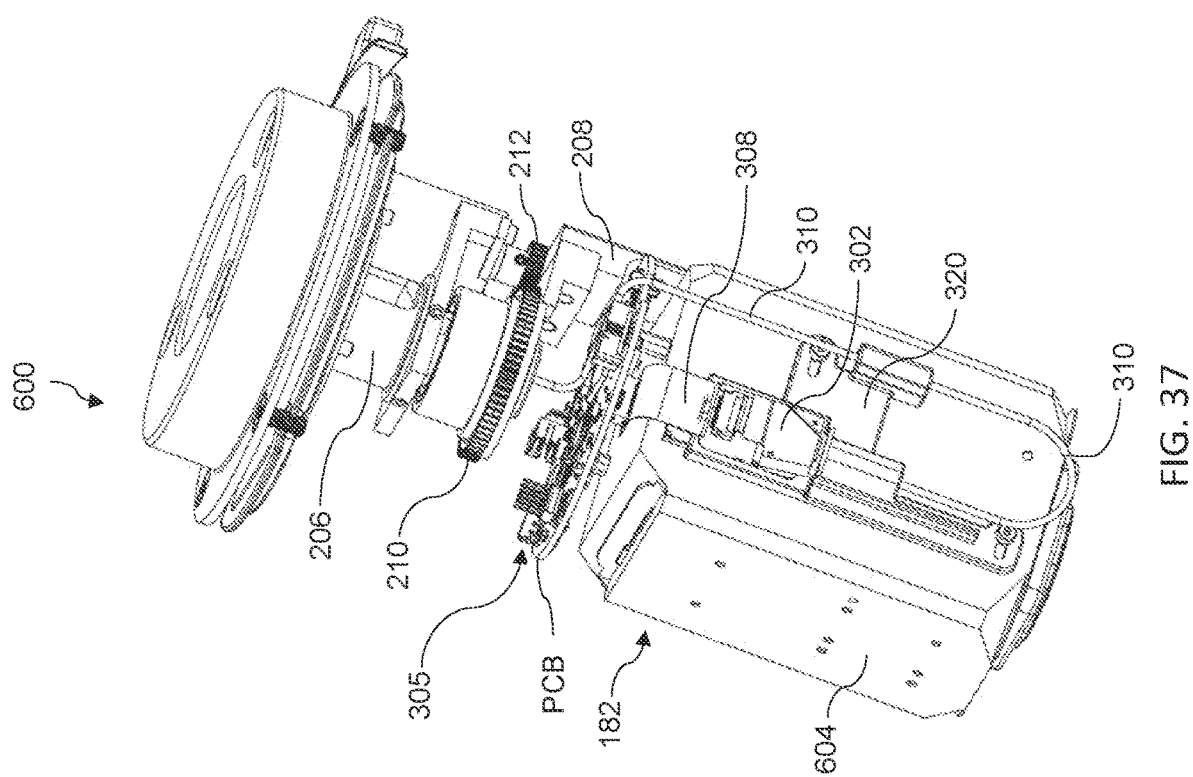
FIG. 37
FIG. 38

LIGHT HEAD HAVING CAMERA ASSEMBLY INTEGRATED IN HANDLE AND SURGICAL LIGHTING SYSTEM INCLUDING SAME

This application claims priority to U.S. Patent Application No. 63/000,672 filed Mar. 27, 2020; U.S. Patent Application No. 63/000,655 filed Mar. 27, 2020; and U.S. Patent Application No. 63,000,719 filed Mar. 27, 2020. These prior applications are incorporated herein by reference.

FIELD OF THE INVENTION

The technology of the present disclosure relates generally to a surgical lighting system, and more specifically to a light head for a medical device support system, suspension system, and/or carry system including a camera assembly.

BACKGROUND

Light heads for medical device support systems, suspension systems and/or other carry systems, are used in health treatment settings such as hospital examination rooms, clinics, surgery rooms and emergency rooms to illuminate a region of interest (e.g., surgical treatment site or other medical site) below or proximate the light head. The light heads typically include a housing, one or more light emitting elements mounted inside the housing, and a handle mounted to the housing to enable a healthcare professional or other individual to adjust the position of the light head according to the needs of a specific medical procedure. The handle is typically formed to have an ergonomic structure that enables a user to wrap a hand around the handle such that the internal space within the handle is limited.

In these health treatment settings, there is often a need to capture and/or record images or video of the region of interest. The images or video may be used for various purposes, such as a visual aid in performing a given procedure. One or more cameras may be included as a part of the medical device support system, suspension system and/or other carry system. For example, a camera may be mounted in the handle of the light head and arranged to capture images of the region of interest that is illuminated by the one or more light emitting elements of the light head. However, the type of camera used in the handle of the light head has been limited due to issues of adjustability and/or reliability of the camera, particularly in view of the limited space within the handle.

Further, a sterile handle in a surgical environment has ergonomic needs whereby a too large handle may be undesirable and, in some cases, unacceptable.

Accordingly, there remains a need for further contributions in this area of technology.

SUMMARY OF INVENTION

The present disclosure relates to a camera assembly arranged in a surgical light head handle. An exemplary application of the surgical light head includes a surgical light such as those used in operating rooms to provide increased light to a specific area of the room (e.g., a region of interest). Embodiments of the present disclosure allow for integration of fiber optic capability into the light head handle for transmission of an optical video signal from the camera in the handle to the light head housing. Embodiments of the present disclosure also provide for thermal management of heat generated in connection with one or more components of the fiber optic assembly.

According to one aspect of the invention, a surgical lighting system includes a light head housing including a plurality of light emitting elements therein that are arranged to emit light downward to a region of interest; a handle mounted to the light head housing and protruding downward from the light head housing, the handle including a handle housing having a sufficient size to be gripped by the human hand; a camera mounted within the handle housing, the camera having a field of view that encompasses at least a portion of the region of interest; and an optical fiber cable that extends from a location within the handle housing and to the light head housing, the optical fiber cable being configured to transmit optical video signals associated with video data captured by the camera to the light head housing.

Embodiments of the invention may include one or more of the following additional features separately or in combination.

The surgical lighting system may further include a fiber module within the handle housing and coupled to the optical fiber cable, wherein the fiber module may be configured to convert electrical video signals of video data captured by the camera into the optical video signals.

The surgical lighting system may further include a bracket that retains the fiber module in a fixed position relative to the camera.

The bracket may include a fiber module retention channel and the fiber module may include a flange that slidably fits into the fiber module retention channel.

The bracket may include a retention wall that holds the fiber module against a camera assembly including the camera.

The camera assembly may include a heat transfer plate in heat transmissive contact with the fiber module to draw heat away from the fiber module.

The retention wall of the bracket may hold the fiber module against the heat transfer plate.

The surgical lighting system may further include a heat transfer pad sandwiched between the fiber module and the heat transfer plate, wherein the bracket compresses the heat transfer pad between the fiber module and the heat transfer plate.

A distal end of the optical fiber cable may have a ferrule and the bracket may include an interface channel within which the ferrule seats to align the distal end of the optical fiber cable with an optical video signal transmission port of the fiber module.

The bracket may include a biasing member that exerts a continuous force against the ferrule to compress the distal end of the optical fiber cable against the optical video signal transmission port of the fiber module.

The interface channel may have at its opposite ends a distal wall and the fiber module respectively, and the biasing member may have a first end that exerts the continuous force against the ferrule and a second end that abuts the distal wall.

The bracket may include a guide channel that guides the optical fiber cable within the handle housing and to the light head housing.

The optical fiber cable may have a bend radius as it passes between the distal wall and the light head housing.

The bracket may include a receptacle that includes a first wall and a second wall opposite the first wall, wherein a ferrule and a biasing member are coupled to the optical fiber cable at a distal end of the optical fiber cable, and wherein the biasing member has a first end that exerts a continuous force against the ferrule and a second end that abuts the first wall.

The bracket may include an interface channel including a bottom wall and side walls, the interface channel extending between a proximal end and a distal end in a first direction, a distal wall located at the distal end of the interface channel and extending between the side walls, the distal wall comprising a slot providing fluid communication through the distal wall, the retention wall and fiber module retention channel located at the proximal end of the interface channel, the fiber module retention channel extending between a proximal end and a distal end in a second direction orthogonal to the first direction.

A ferrule and a biasing member may be coupled to the optical fiber cable at a distal end of the optical fiber cable, and the biasing member may exert a continuous force against the ferrule and the distal wall to position the distal end of the optical fiber cable against an optical video signal transmission port of the fiber module.

The fiber module may include a tubular interface member, and the ferrule may be in contact with a distal end of the tubular interface member.

A distal end of the optical fiber cable may be laterally aligned with an axis of the optical video signal transmission port of the fiber module.

A distal end of the optical fiber cable may be angularly aligned with an axis of the optical video signal transmission port of the fiber module.

The bracket may further include a cable retention channel that guides the optical fiber cable within the handle housing.

The interface channel and the cable retention channel may extend parallel to one another.

The cable retention channel may include a linear portion and a curved portion having a predetermined radius of curvature.

The optical fiber cable may extend from the interface channel and may be routed through the cable retention channel, and a portion of the optical fiber cable between the interface channel and the cable retention channel may have a predetermined radius of curvature.

A portion of the optical fiber cable in the handle housing may be bent at a predetermined radius of curvature.

The camera may be mounted within the handle housing for rotation within the handle housing about a rotation axis.

The fiber module may be disposed laterally to the side of and in spaced relationship relative the camera radially outward from the rotation axis of the camera.

The fiber module may be disposed between the camera and the inner perimeter of the handle housing.

The light head housing may be coupled to a distal end of an arm that is mounted for pivotable movement to a shaft.

According to one aspect of the invention, a surgical lighting system includes a light head housing including a plurality of light emitting elements therein that are arranged to emit light downward to a region of interest; a handle mounted to the light head housing and protruding downward from the light head housing, the handle including a handle housing having a sufficient size to be gripped by the human hand; and a camera mounted within the handle housing, the camera having a field of view that encompasses at least a portion of the region of interest; wherein the handle housing has an upper generally tubular section mounted to the light head housing and a lower generally tubular section extending downward from a bottom of the upper generally tubular section, the outer perimeter of the lower generally tubular section being relatively wider in axial cross section than the outer perimeter of the upper generally tubular section over a portion of the upper generally tubular section.

Embodiments of the invention may include one or more of the following additional features separately or in combination.

The lower generally tubular section may be cylindrical in shape.

The upper generally tubular section may be generally square tubular in shape with curved corners.

The lower generally tubular section may be cylindrical in shape, the upper generally tubular section may be generally square tubular in shape with curved corners, and the width in axial cross section of the lower generally tubular section where the lower generally tubular section transitions to the upper generally tubular section may be equal to the width in axial cross section of the upper generally tubular section at the curved corners.

The upper generally tubular section may include buttons for controlling attributes of the emitted light from the light head.

A bottom of the lower generally tubular section may be open downward and the camera may be sized for insertion through the open bottom to within the handle housing and axially above the open bottom.

The surgical lighting system may further include a cap removably mounted to the bottom of the lower generally tubular section to close the open bottom in the lower generally tubular section.

A bottom of the lower generally tubular section may include a cylindrical shape threaded region and the cap may include a round shape mating threaded region, and the cap may be removably mounted to the bottom of the lower generally tubular section by engagement between the round shape mating threaded region of the cap and the cylindrical shape threaded region of the bottom of the lower generally tubular section.

An inner perimeter of the lower generally tubular section may be relatively wider in axial cross section than an inner perimeter of the upper generally tubular section.

The surgical lighting system may further include a shoulder that transitions radially outwardly from the inner perimeter of the upper generally tubular section to the inner perimeter of the lower generally tubular section.

The camera may be relatively wider in axial cross section than the width of an inner perimeter of the upper generally tubular section and the camera may be relatively narrower in axial cross section than the width of an inner perimeter of the lower generally tubular section.

The camera may be configured to be inserted into and contained within an inner perimeter of the lower generally tubular section but not into or within an inner perimeter of the upper generally tubular section.

The surgical lighting system may further include a single printed circuit board (PCB) disposed in the handle housing.

The single PCB may be relatively narrower in axial cross section than the width of an inner perimeter of the upper generally tubular section.

These and further features will be apparent with reference to the following description and attached drawings which set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings. The invention includes all changes, modifications and equivalents coming within the spirit and terms of the claims appended hereto.

Features that are described and/or illustrated with respect to one embodiment may be used in the same way or in a similar way in one or more other embodiments and/or in combination with or instead of the features of the other embodiments.

BRIEF DESCRIPTION OF THE DRAWINGS

The annexed drawings, which are not necessarily to scale, show various aspects of the present disclosure.

FIG. 11 is a front elevation view of the bracket of FIG. 9.

FIG. 12 is a rear elevation view of the bracket of FIG. 9.

FIG. 22 is a front elevation view of the bracket of FIG. 20.

FIG. 23 is a rear elevation view of the bracket of FIG. 20.

FIG. 37 is an exploded perspective view of parts of the handle of FIG. 24 with the handle housing removed.

FIG. 38 is a cross section view of the handle of FIG. 24.

DETAILED DESCRIPTION

Figure 1:
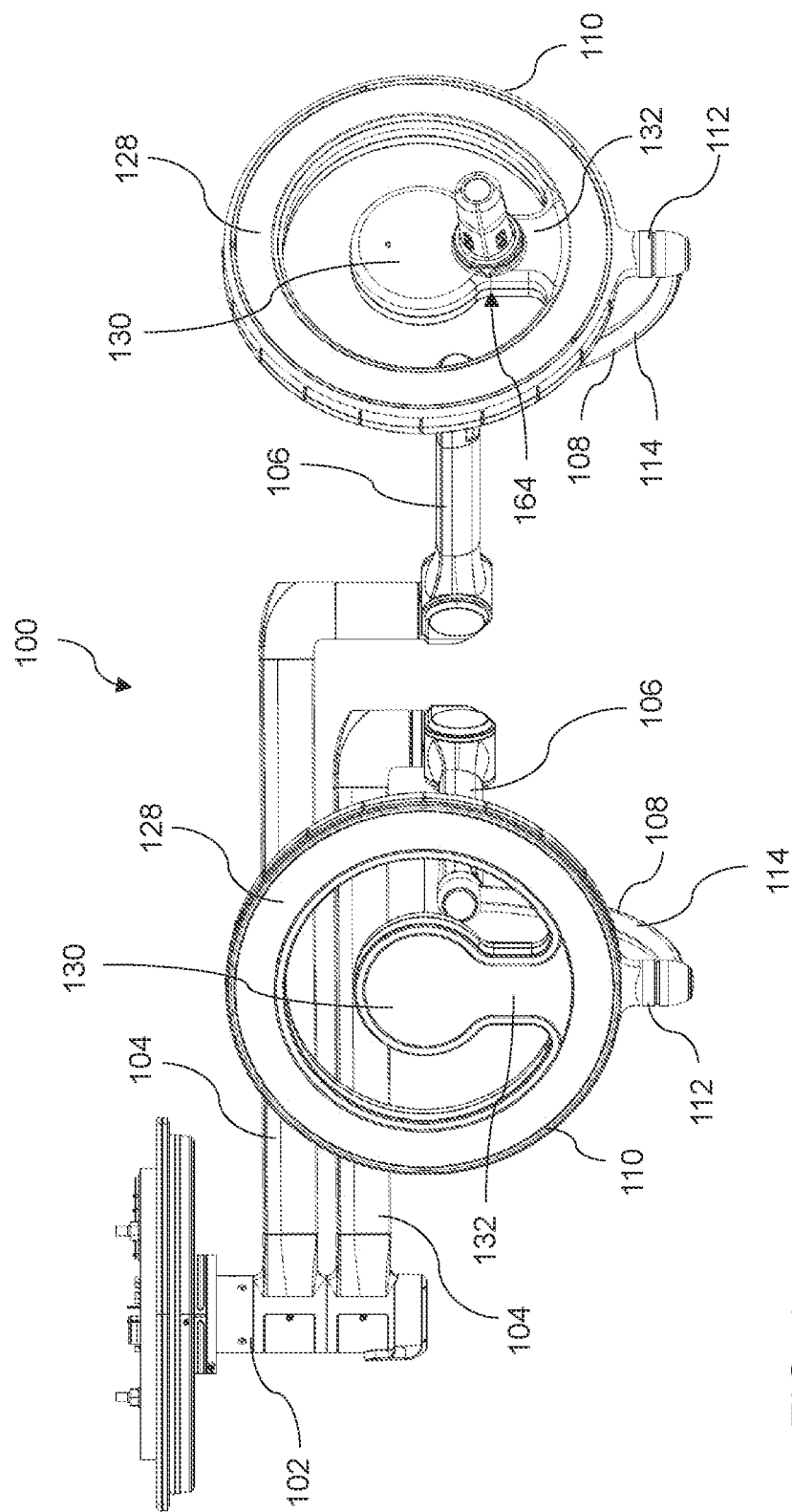
FIG. 1 is a side elevation view of an overall configuration of a medical device support system in accordance with an embodiment of the present disclosure, showing a top of a left positioned light head and a bottom of a right positioned light head.

For the purpose of promoting an understanding of the principles of the present disclosure, reference will now be made to the embodiments illustrated in the drawings and specific language will be used to describe the same. It will nevertheless be understood that no limitation of the scope of the present disclosure is thereby intended. The figures are not necessarily to scale. Features that are described and/or illustrated with respect to one embodiment may be used in the same way or in a similar way in one or more other embodiments and/or in combination with or instead of the features of the other embodiments. Any alterations and further modifications of the described embodiments, and any further applications of the principles of the present disclosure as described herein, are contemplated as would normally occur to one skilled in the art to which the present disclosure relates.

With reference to FIG. 1, an exemplary medical device support system is shown at 100. The medical device support system 100 includes a central shaft or support column 102 that is suspended from the ceiling, and two generally horizontal extension arms 104 mounted to the shaft 102 for rotational movement about the central shaft 102. In other implementations, the central shaft 102 could be mounted to a wall or stand rather than the ceiling. Two load balancing arms 106 are pivotably mounted to the distal ends of the respective extension arms 104. Yoke assemblies 108 are mounted to the distal ends of the respective load balancing arms 106. The yoke assemblies 108, in turn, support respective light heads 110 for multi-axis movement relative to the load balancing arms 106. Each light head 110 includes a bushing or other coupling member 112 that rotatably connects the light head 110 to the distal end of an arm 114 of a respective yoke assembly 108, as shown. The load balancing arms 106 and yoke assemblies 108 enable positioning of the light heads 110 to a desired orientation relative to, for example, a patient operating table and healthcare professionals in the operating room.

The exemplary medical device support system shown in FIG. 1 includes two light heads 110, each mounted to a respective extension arm 104, load balancing arm 106, and yoke assembly 108. It will be appreciated that in other embodiments, the medical device support system may include more or fewer light heads. It will also be appreciated that the medical device support system may include other accessories mounted to the central shaft 102.

Figure 2:
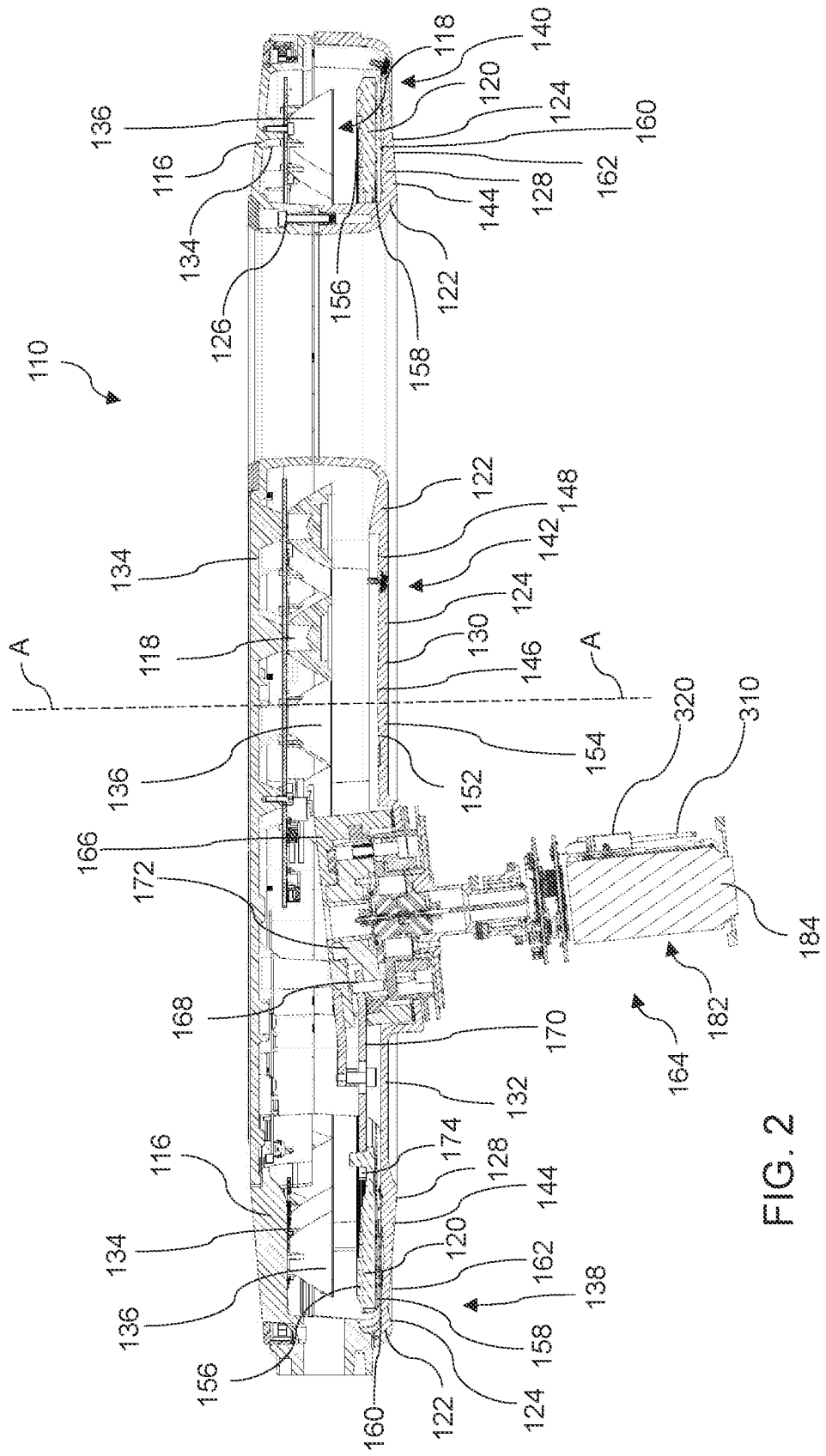
FIG. 2 is a side cross section view of a light head in accordance with an embodiment of the present disclosure, showing a housing base, a housing cover, and internal components of the light head and handle.

With additional reference to FIG. 2, each light head 110 of the system 100 includes a housing base 116, a plurality of light emitting elements 118, an annular shape lens 120, and a housing cover 122 including a housing lens 124. The housing base 116 and the housing cover 122 are connected by fasteners 126. The annular shape lens 120 and the housing lens 124 are in a light emitting path of the plurality of light emitting elements 118.

As shown in FIGS. 1 and 2, each light head 110 includes an annular shape outer portion 128, an inner round portion 130, and a radially protruding arm 132 that connects the annular shape outer portion 128 to the inner round portion 130. In the illustrative embodiment, the radially protruding arm 132 arranges the annular shape outer portion 128 and the inner round portion 130 in concentric relation to one another, and in concentric relation to the rotation axis A-A of the annular shape lens 120. The radially protruding arm 132 also houses one or more components for transferring rotational motion from a handle 164 mounted to the light head housing 116, 122 of the light head 110 to the annular shape lens 120 of the light head 110 (described in more detail below). It will be appreciated that the annular shape outer portion 128 and the inner round portion 130 need not be in concentric relation to one another and instead can be arranged by the protruding arm in eccentric relation to one another. It will further be appreciated that in an alternate embodiment the inner round portion 130 of the light head 110 may be omitted; and in such form, only the annular shape outer portion 128 emits light to the region of interest (e.g., surgical treatment site or other medical site) below or proximate the light head.

As shown in FIG. 2, an inside surface 134 of the housing base 116 supports the plurality of light emitting elements 118. The light emitting elements 118 may in some embodiments include one or more solid-state light emitters. Exemplary solid-state light emitters include such devices as light emitting diodes (LEDs), laser diodes, and organic LEDs (OLEDs). The LEDs may be broad spectrum LEDs (e.g., white light emitters) or LEDs that emit light of a desired color or spectrum (e.g., red light, green light, blue light, or ultraviolet light). In other embodiments, the LEDs may be a mixture of broad-spectrum LEDs and LEDs that emit narrow-band light of a desired color, or a mixture of LEDs that emit different respective colors or spectrum. In some embodiments, the solid-state light emitters constituting the light emitting elements 118 all generate light having the same nominal spectrum. In other embodiments, at least some of the solid-state light emitters constituting the light emitting elements 118 generate light that differs in spectrum from the light generated by the remaining solid-state light emitters. In other embodiments, the light emitting elements 118 may include one or more other types of light sources. Non-limiting examples of light sources include halogen, fluorescent, compact fluorescent, incandescent, and the like. In still other embodiments, the light emitting elements 118 may include a combination of solid-state light emitters and one or more of the above other types of light sources.

Figure 8:
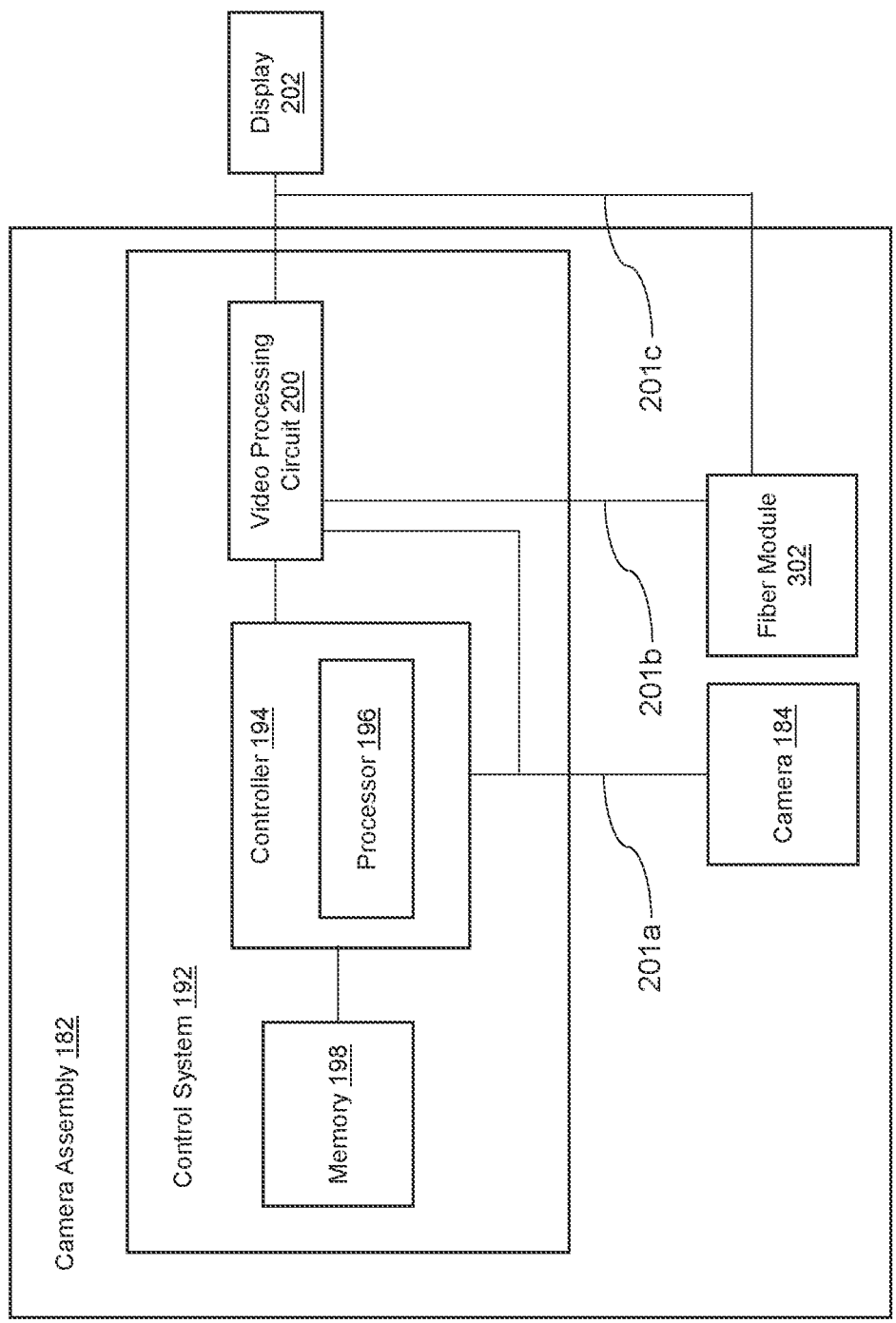
FIG. 8 is a schematic view of exemplary control system and display coupled to the camera assembly.
Figure 9:
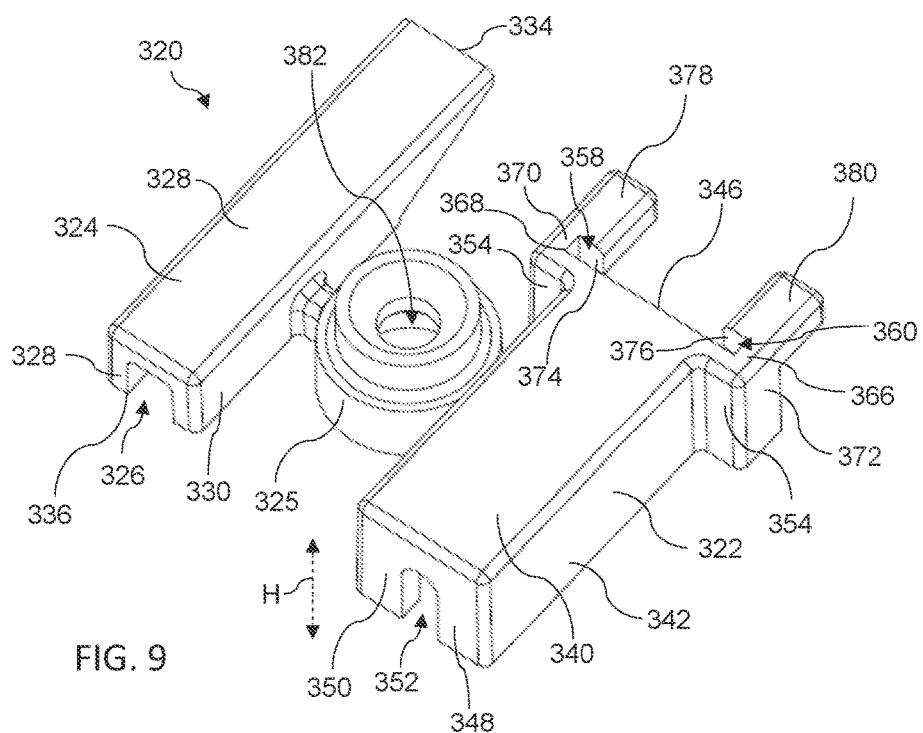
FIG. 9 is a front perspective view of a bracket in accordance with an embodiment of the present disclosure.
Figure 10:
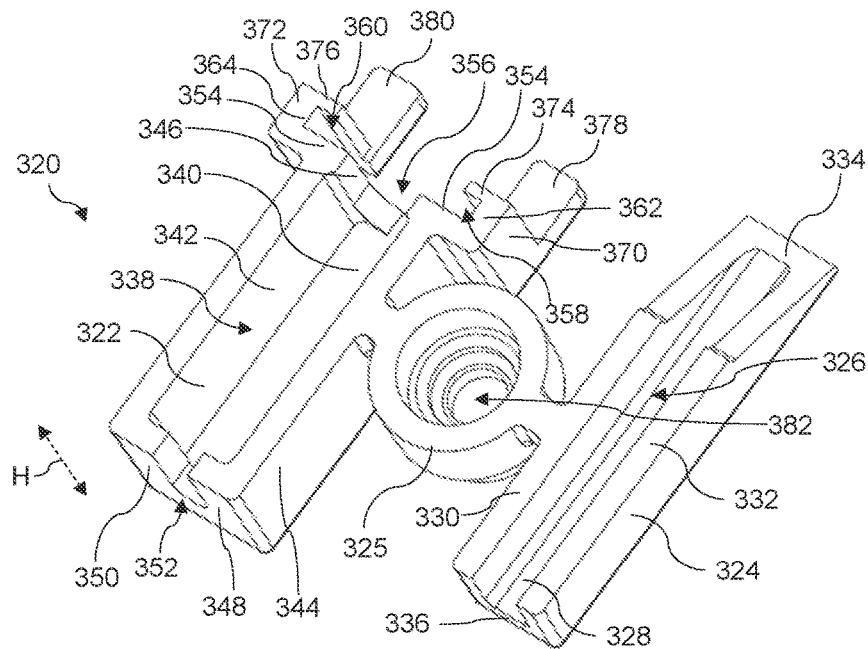
FIG. 10 is a rear perspective view of the bracket of FIG. 9.

A controller controls the light emitting elements 118 of the annular shape outer portion 128 and the inner round portion 130 to emit light to a region of interest (e.g., surgical treatment site or other medical site) below or proximate the light head 110. For example, a controller may control the light sources 118 of the annular shape outer portion 128 and the inner portion 130 to emit light to a region of interest below the light head 100. Control of the respective light sources 118 may be performed, for example, collectively, individually, in groups, by section, or in any other suitable manner. In some embodiments, the controller may be provided as part of the light head 110 such as shown in FIG. 8 where the controller is part of a camera assembly 182 within the handle 164 of the light head 110. In other embodiments, the controller may be implemented elsewhere in the medical device support system 100 external to the camera assembly 182, for example elsewhere in the light head 110 or external to the light head 110, or the controller may be implement external to the medical device support system 100.

With continued reference to FIG. 2, a plurality of collimators 136 are mounted to the inside surface 134 of the housing base 116 and in the light emitting paths of the respective plurality of light emitting elements 118. Each collimator may be associated with a respective light emitting element 118 and may be arranged such that at least a portion of the light emitted from the associated light emitting element 118 is incident a surface of the collimator. The collimators 136 collect and direct, and/or collimate, the light emitted from the associated light emitting element 118 into a narrowed beam. In one form, the collimators 136 may comprise total internal reflection (TIR) lenses. In some embodiments, the collimators 136 and associated light emitting elements 118 may be grouped together in modules 138, 140 mounted to the inside surface of the annular shape outer base 128, and one round module 142 mounted to the inside surface of the inner round base 130.

The housing cover 122 also includes the housing lens 124, which in the illustrative embodiment includes an annular shape outer cover 144 and an inner round cover 146. Both the annular shape outer cover 144 and an inner round cover 146 may be shaped to redirect light emitted from the light emitting elements and passing therethrough. In an alternate form, the housing cover 122 is configured such that one or both of the annular shape outer cover 144 and an inner round cover 146 are formed of a transparent non-lens material, i.e. a non-light bending material. In embodiments where both the annular shape outer cover 144 and an inner round cover 146 are formed of a transparent non-lens material, the housing lens 124 may be considered to be omitted from the light head 110.

FIG. 2 shows an axial arrangement of the light emitting elements 118, the collimators 136, the annular shape lens 120, and the housing lens 124, where axial refers to the direction of emission of light from the light head 110, or downward in FIG. 2. The annular shape outer cover 144 and the inner round cover 146 are in the light emitting paths of respective ones of the plurality of light emitting elements 118. The annular shape lens 120 is in the respective light emitting paths of respective ones of the plurality of light emitting elements 118, positioned between the light emitting elements 118 and the annular shape outer cover 144. Each collimator 136 is also arranged in the light emitting path of a respective light emitting element of the plurality of light emitting elements 118 in the annular shape outer portion 128 of the light head 110 positioned between the light emitting element 118 and the annular shape lens 120; or is arranged in the light emitting path of a respective light emitting element of the plurality of light emitting elements 118 in the inner round portion 130 of the light head 110 positioned between the light emitting elements 118 and the inner round cover 146.

The annular shape lens 120, the housing lens 124, and the collimators 136, if provided, can take on any form for spreading and/or bending the light emitted by the light emitting elements 118. As shown for example in FIG. 2, the inner round cover 146 of the housing lens 124 has a top face 152 formed as a stepped surface, for example a plurality of Fresnel wedges, that bends individual portions of the light beams, and a bottom face 154 formed as a generally planar surface. The annular shape lens 120 has a top face 156 formed as a stepped surface, for example a plurality of Fresnel wedges, that bends individual portions of the light beams, and a bottom face 158 formed as a wavy or curved surface that bends individual portions of the light beams. The annular shape outer lens 144 of the housing lens 124, has a top face 160 formed as a wavy or curved surface and a bottom face 162 formed as a generally planar wedge-shaped surface, where a generally planar wedge-shaped surface refers to a generally planar surface that is not perpendicular to the direction of travel of the light beam emitted by the light emitting elements 118 and collimators 136, for example.

With continued reference to FIGS. 1 and 2, the light head 110 includes a handle 164. In the exemplary embodiment, the handle 164 is rotatably mounted coaxially to a hub 166 of the light head 110. A lever 170 is provided for transferring rotational motion from the handle 164 to the annular shape lens 120. A first end 168 of the lever 170 is movably coupled to a bushing 172 of the handle 164 and a second end 174 of the lever 170 is movably coupled to the annular shape lens 120. The lever 170 is configured to transfer rotational motion of the handle 164 at the first end 168 of the lever 170 into rotational motion of the annular shape lens 120 at the second end 174 of the lever 170. It will be appreciated that in other embodiments, the handle 164 may be mounted in a stationary manner, although components within the handle 164, for example a camera assembly 182 described below, may be configured to rotate therein. Further details of an exemplary surgical light system suitable for the present application are described in U.S. application Ser. No. 17/151,760 filed Jan. 19, 2021, and titled "Lighthead with Rotating Lens Assembly and Method of Operating Same," which is incorporated by reference for all purposes as if fully set forth herein.

Figure 3:
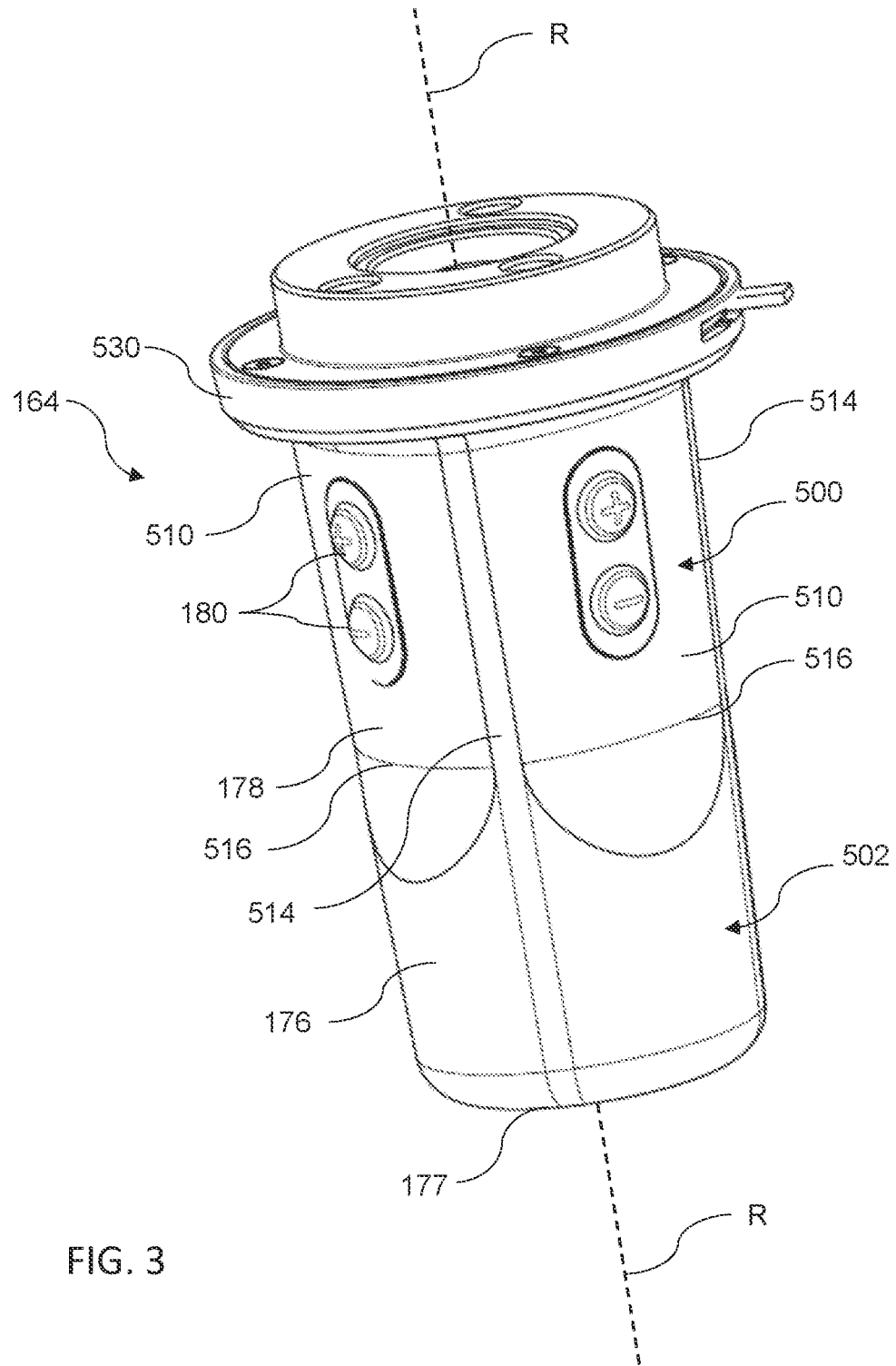
FIG. 3 is a perspective side view of a handle in accordance with an embodiment of the present disclosure having a handle housing including a grip portion.

FIGS. 3-6 show further details of the handle 164. FIG. 3 shows the handle 164 having the grip portion 178 of the handle housing 176 having buttons 180 that provide a user interface for the handle 164 for controlling attributes of the emitted light from the light head 110. In other embodiments, the handle 164 may be provided with buttons that interface with a drive motor to rotate the afore mentioned camera assembly 182 within the handle housing 176. The handle housing 176, including the grip portion 178 thereof, has a sufficient size to be gripped by a human hand meaning that the outermost diameter or perimeter of the handle housing 176 is selected to enable a human hand to be comfortably wrapped around the handle housing 176. The handle housing 176 may be cylindrical in shape and elongated along a rotation axis R. Other shapes may be suitable for the handle housing 176 as will be described in greater detail below.

Figure 4:
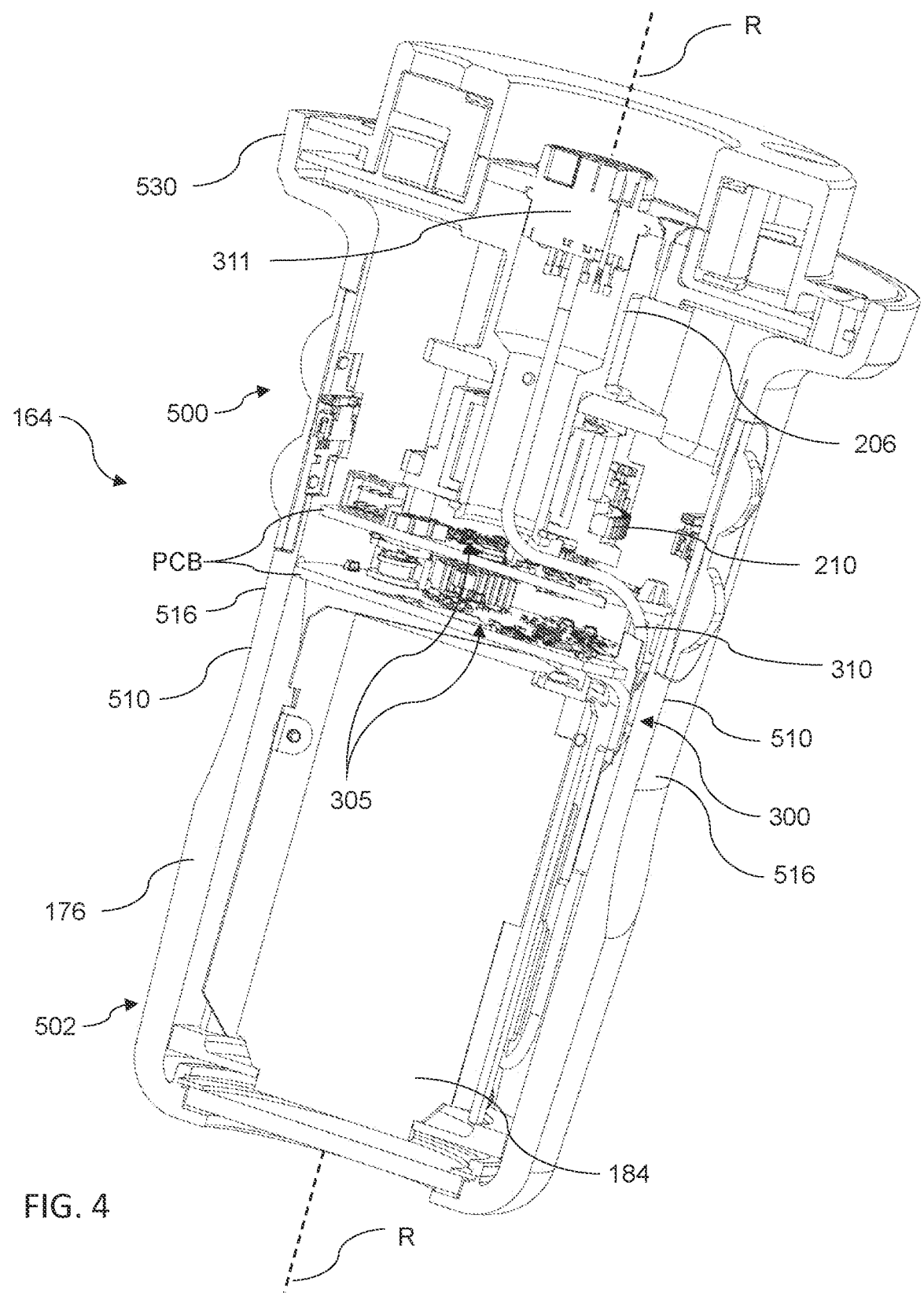
FIG. 4 is a perspective cross section view of the handle of FIG. 3.
Figure 5:
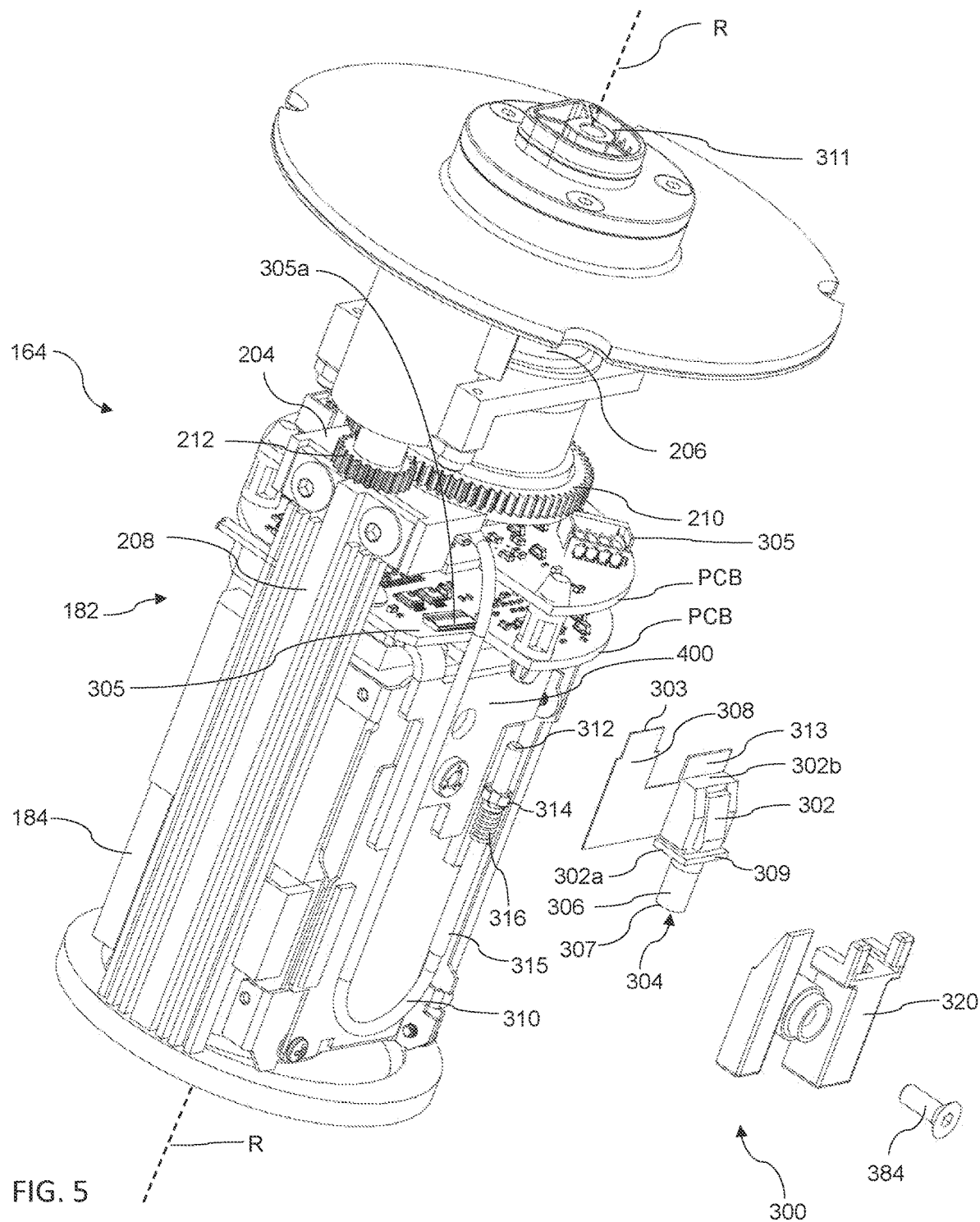
FIG. 5 is an exploded perspective view of parts of the handle of FIG. 3 with the handle housing removed.

FIG. 4 shows a perspective cross section view of the handle 164 and FIG. 5 shows a perspective cross section view of the handle 164 with the handle housing 176 removed. The handle 164 includes a camera assembly 182 within the handle housing 176. The camera assembly 182 includes a camera 184 configured to capture images and/or video of a field of view 186, which may include a target. The target may constitute a region of interest.

Figure 7:
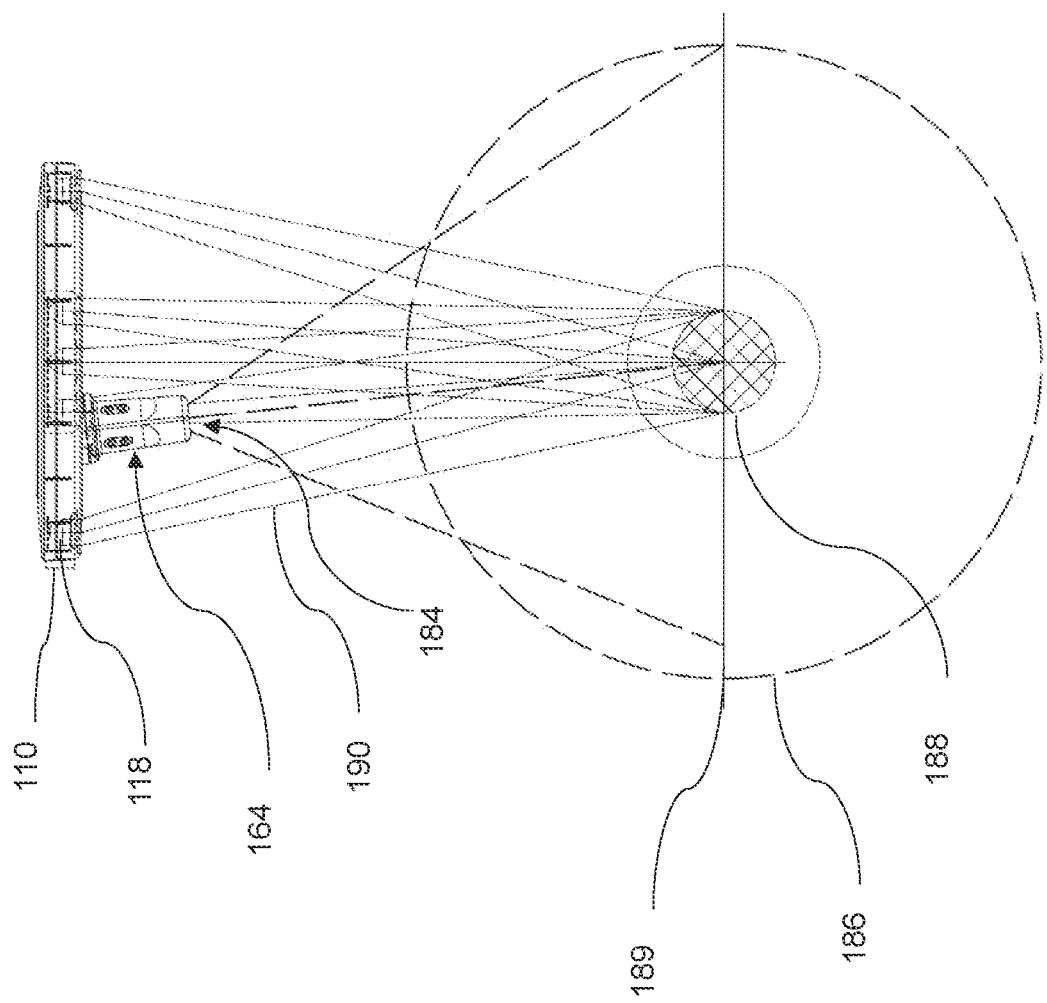
FIG. 7 shows a region of interest illuminated by a light head and a field of view of a camera in the handle of the light head.

As shown in FIG. 7, the region of interest 188 may at least partially be illuminated by light emitted by the plurality of light emitting elements 118. The region of interest 188 may include a specific target, such as a patient on a surgical table 189. A target may be defined as an area which the user intends to illuminate by aiming the light 190 produced by the surgical light. The region of interest 188 may in some embodiments be defined as the area that is illuminated 30 by the light head 110. The region of interest 188 may be formed by the light emitting elements 118 that emit light and collimators and/or lenses that aim, redirect, spread, converge, and or focus the light. The light head may be arranged such that it is a predetermined distance from the region of interest. Adjustment of the light head relative to the region of interest may be performed using the extension arm 104, load balancing arm 106, and/or yoke assembly 108. In an example, the light head may be adjusted such that it is a distance of about one meter from the region of interest. "Target", "region of interest," "target region", and "target region of interest," etc. may be used with reference to the same area.

The camera 184 may include any suitable optical camera including a sensor and being configured to capture images within the region of interest 188. For example, the camera 184 may include a complementary metal oxide semiconductor (CMOS) sensor. Other sensors may be suitable. In an exemplary embodiment, a CMOS sensor having approximately a 2,000,000 pixel resolution, for example an HD camera, may be suitable. It will be appreciated that higher resolution cameras are also contemplated, for example, a 4K camera having for example approximately 9,000,000 pixel resolution, and still further an 8K camera having an even greater pixel resolution. The camera 184 may have any suitable focal distance range, such as between 10 and 1500 millimeters. In one embodiment, an 800 millimeter range may be suitable, for example, for full optical zoom. The camera 184 may have any suitable signal-to-noise ratio. The signal-to-noise ratio may exceed 50 decibels to provide clear images. As will be described in greater detail below, the optical video signal associated with video data captured by the camera 184 and output by the camera assembly 182 utilizes an optical fiber cable 310 that enables a high bandwidth data link so that advantageously the optical video signal is uncompressed, thereby mitigating for example issues such as visual compression artifacts, noise, and video latency. In another exemplary embodiment, the camera 184 may include a surgical display having a resolution that is approximately 4096 by 2160, an aspect ratio of 1.9 to 1, and a viewing angle that is approximately 178 degrees. The camera 184 may also include one or more lenses (not shown) to provide zooming and focusing functionality, as well as any other components to allow for operation of the camera 184. Many other cameras may be suitable.

Referring to FIG. 8, the camera assembly 182 is configured to output an optical video signal pertaining to images and/or video captured by the camera 184 within the field of view 186 and the region of interest 188. The optical video signal may be output from the camera assembly 182 to elsewhere in the medical device support system 100. As will be described in greater detail below, the camera assembly 182 may include a control system 192 that processes image data captured from the camera 184. The control system 192 may be located in the handle housing 176, for example as part of the camera assembly 182 as shown in FIGS. 5 and 8, or in the light head housing 116, 122 of the light head 110, or outside of the light head housing 116, 122, or even outside of the medical device support system 100, or may be located in a combination of two or more of the handle housing 176, the light head housing 116, 122, outside of the light head housing 116, 122, and outside of the medical device support system 100. In the illustrative embodiment, and as will be described in greater detail below, the control system 192 components, i.e. controller 194, processor 196, memory 198, and video processing circuit 200, are part of control electronics 305 of the camera assembly 182. As will also be described below, the control system 192 may be configured to control other components, such as a video display monitor, of the medical device support system 100 in addition to the camera assembly 182.

The control system 192 may include a controller 194 that is configured to carry out overall control of the functions and operations of the control system 192. The controller 194 may include a processor 196, such as a central processing unit (CPU), microcontroller, or microprocessor. The processor 196 executes code stored in a memory (not shown) within the controller 194 and/or in a separate memory, such as the memory 198, in order to carry out operation of the control system 192.

The controller 194 may be coupled to a video processing circuit 200. The video processing circuit 200 may process communications (COMM), power, and a low voltage differential signaling (LVDS) video signal 201a from the camera 184 to create a High-Definition Multimedia Interface (HDMI) format electrical video signal 201b, which electrical video signal may then be processed by a fiber module 302 into an optical video signal 201c used to drive a display 202, for example a display monitor. The fiber module 302 may constitute part of the camera assembly 182 as shown in block diagram in FIG. 8, or may be mounted to the camera assembly 182 as described in greater detail below.

The video processing circuit 200 may also be configured to convert image and/or video data to an image and/or video signal used to drive the display 202. The video processing circuit 200 may include any appropriate buffers, decoders, video data processors and so forth. The optical video signal of the camera assembly 182 may be processed by the controller 194 and/or converted by the video processing circuit 200 and may be displayed on the display 202. The optical video signal of the camera assembly 182 may also or alternatively be stored on a memory, such as the memory 198. The stored image(s) and/or video may be displayed on the display at a later time.

The display 202 may be used to present images and/or video to a user (e.g., healthcare professional or other individual), as well as any other graphics or information to the user. The display may be a lighted display. In some embodiments, the display 202 is a backlit liquid-crystal display (LCD). The LCD may be backlit using one or more suitable light sources (e.g., a light emitting diode (LED), cold cathode fluorescent (CCFL), etc.). In other embodiments, the display 202 is an organic light-emitting diode (OLED) display.

With continued reference to FIGS. 2 and 4-6, the camera assembly 182 may be configured for rotation about the rotation axis R in both a clockwise direction and in a counterclockwise direction. The camera assembly 182 includes a bracket 204, a spindle 206, and an axially extending bracket 208. The spindle 206 is fixed relative to the handle housing 176 of the handle 164. The bracket 204 is rotatably mounted to the spindle 206 and is fixed to the axially extending bracket 208. In the illustrative embodiment, the brackets 204, 208 together form a rotatable bracket 204, 208 having an inverted L shape. The rotatable bracket 204, 208 provides for rotation of the camera 184 within the handle housing 176 (e.g., rotation about the rotation axis R). A gear 210 is fixed to the bracket 204 and a pinion 212 is in meshing engagement with the gear 210 for driving the gear 210 and thus the rotatable bracket 204, 208 to rotate the camera 184. The camera assembly 182 may in some embodiments be configured for rotation that is greater than 360 degrees about the rotation axis R in both a clockwise direction and in a counterclockwise direction. Further details of an exemplary means of providing rotational capability of the camera assembly 182 within the handle housing 176 is described in U.S. Provisional Application No. 63/000,655 filed Mar. 27, 2020, titled "360 Degrees Plus Rotation Module for Surgical Light Head Handle," which is incorporated by reference for all purposes as if fully set forth herein. Many other rotation assemblies, if included, may be suitable.

The camera assembly 182 of the present disclosure may include a fiber optic assembly 300 that provides fiber optic capability integrated into the light head handle 164 for transmission of the optical video signal associated with video data captured by the camera 184 from a location within the handle 164 to the light head housing 116, 122. In some embodiments, the optical video signal may also be transmitted from the light head housing 116, 122 to elsewhere in the medical device support system 100.

Figure 6:
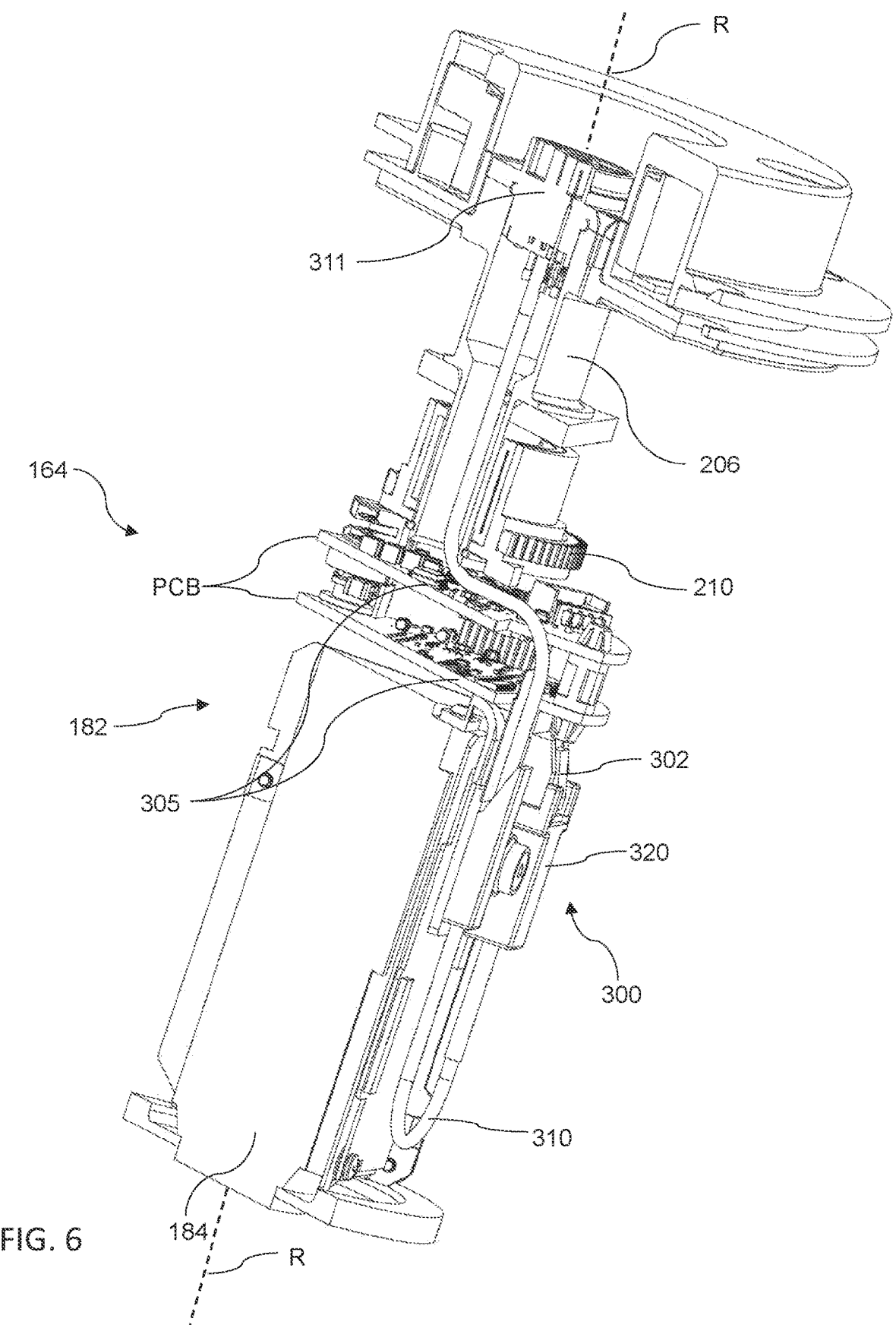
FIG. 6 is a perspective cross section view of parts of the handle of FIG. 3 with the handle housing removed.

With reference to FIGS. 5 and 6, the fiber optic assembly 300 includes a fiber module 302 located within the handle housing 176 and coupled to the camera assembly 182, for example, coupled to a heat transfer plate 400 thereof, as will be described in greater detail below. The fiber module 302 is configured to convert electrical video signals of video data captured by the camera 184 into optical video signals. The fiber module 302 includes an optical video signal transmission port 304. A tubular interface member 306 is coupled to the optical video signal transmission port 304 and is configured to mate with an optical fiber cable 310.

In the illustrated embodiment, a flexible ribbon cable 308 is coupled to the fiber module 302. An opposite end 303 of the flexible ribbon cable 308 (that is, the end 303 opposite to where the flexible ribbon cable 308 is coupled to the fiber module 302) may be connected to the camera assembly 182, for example, control electronics 305 such as a printed circuit board (PCB) of the camera assembly 182. For example, the opposite end 303 of the flexible ribbon cable 308 can be plugged into a connector 305a of the control electronics 305. In the illustrative embodiment, the control electronics 305 are positioned axially between the camera 184 and the gear/pinion arrangement 210, 212 of the camera assembly 182. In some embodiments, the control electronics 305 may be positioned axially between the camera 184 and the accessory port connector 311 in a position axially above the gear/pinion arrangement 210, 212. In the illustrative embodiment, the control electronics 305 include the components of the control system 192, i.e. the controller 194, processor 196, memory 198, and video processing circuit 200. The camera 184 may be configured to transmit communications (COMM), power, and a low voltage differential signaling (LVDS) video signal for example 201a in FIG. 8 to the control electronics 305. The control electronics 305, for example the video processing circuit 200 of the control system 192 of the control electronics 305, may process the video signal to create a High-Definition Multimedia Interface (HDMI) format electrical video signal for example 201b in FIG. 8 that is transmitted via for example the connector 305a to the flexible ribbon cable 308. The fiber module 302 then converts the HDMI electrical video signal to an HDMI optical video signal for example 201c in FIG. 8.

Referring to FIG. 6, any heat radiated by the fiber module 302 may be transferred to and dissipated by the heat transfer plate 400, as will be described in greater detail below. As shown in FIG. 5, and FIGS. 13-15 to be described in greater detail below, a heat transfer pad 313 may be sandwiched between the fiber module 302 and the heat transfer plate 400 the length of the fiber module 302, that is, to axially opposite ends 302a, 302b of the fiber module 302, and slightly beyond the end 302b. The heat transfer pad 313 may be made of any suitable compressible material, for example, a silicone polymer material, or other conformable, thermally conductive material for filling air gaps, including gap fillers, thermal pads, form-in-place pads, sil pads, among others. The fiber module 302 may be mounted to the heat transfer plate 400 by a clamping force of the bracket 320, with the heat transfer pad 313 (if provided) compressed therebetween.

The fiber optic assembly 300 further includes an optical fiber cable 310. The optical fiber cable 310 may transmit optical images and/or video signals, for example the afore described HDMI optical video signal 201c, associated with image and/or video data captured by the camera 184. In the illustrative embodiment, the optical fiber cable 310 transmits the optical video signals from the fiber module 302 to elsewhere in the medical device support system 100. The optical fiber cable 310 provides a high bandwidth data link suitable for the optical video signal output associated with the afore mentioned camera 184, whether an HD camera, 4K camera or even 8K camera. In an exemplary embodiment, the optical fiber cable 310 provides a high bandwidth capability for the optical video signal to be uncompressed, thereby mitigating for example issues such as visual compression artifacts, noise, and video latency. With reference to FIG. 8, in some embodiments, the optical fiber cable 310 may be configured to provide a bidirectional control signal or data/COMM link that links the control electronics 305 (in the illustrative embodiment the control system 192) to for example intelligent display devices. Thus, the optical fiber cable 310 may provide a unidirectional control signal in that the optical fiber cable 310 provides an optical video signal to drive for example display 202. The optical fiber cable 310 may provide a bidirectional control signal in that the optical fiber cable 310 provides receive/transmit control signals between the display 202 and the control electronics 305.

The optical fiber cable 310 extends from a location within the handle housing 176, in the illustrative embodiment the location at which the optical fiber cable 310 is attached to the fiber module 302, to the light head housing 116, 122. From the light head housing 116, 122, the optical fiber cable 310 may extend to additional components within the light head housing 116, 122 and/or to, for example, the coupling member 112, the yoke assembly 108, the load balancing arm 106, the extension arm 104, the support column 102, or elsewhere in the medical device support system 100. Additionally, or alternately, and with reference to FIGS. 4-6, 14 and 15, the optical fiber cable 310 may be coupled to a suitable handle-to-light head housing accessory port connector 311 in the light head housing 116, 122, for example at the location where the handle 164 is rotatably mounted coaxially to the hub 166 of the light head 110, and another optical fiber cable may extend from such accessory port connector 311 to additional components within the light head housing 116, 122 and/or to, for example, the coupling member 112, the yoke assembly 108, the load balancing arm 106, the extension arm 104, the support column 102, or elsewhere in the medical device support system 100. In the illustrative embodiment, the accessory port connector 311 integrates an electrical cable connection with the optical fiber cable 310 connection so that electrical signals, for example electrical power and/or electrical data signals, may be transmitted from the light head housing 116, 122, or from elsewhere in the medical device support system 100, to the handle 164 and the camera assembly 182 therein, or vice versa. Other embodiments are also contemplated.

The optical video signal is transmitted via the optical fiber cable 310 and/or any additional or alternate cables, to elsewhere in the medical device support system 100, for example, the display 202. As noted above, the control system 192 for controlling components such as the display 202 may be located in the handle housing 176, for example as part of the camera assembly 182 as shown in FIGS. 5 and 8, or in the light head housing 116, 122 of the light head 110, or outside of the light head housing 116, 122, or even outside of the medical device support system 100, or may be located in a combination of two or more of the handle housing 176, the light head housing 116, 122, outside of the light head housing 116, 122, and outside of the medical device support system 100. Accordingly, the optical fiber cable 310 and/or additional or alternate cables may extend through other components of the medical device support system 100, for example, through the yoke assembly 108, load balancing arm 106, extension arm 104, and support column 102.

In an assembled state, the distal end 312 of the optical fiber cable 310 is optically coupled to the fiber module 302. Optical image and/or video signals from the fiber module 302 are input from the optical video signal transmission port 304 to the distal end 312 of the optical fiber cable 310. The optical fiber cable 310 includes a ferrule 314 and a biasing member 316 proximate the distal end 312 of the optical fiber cable 310. As described below, the ferrule 314 and a biasing member 316 may assist in aligning and retaining the distal end 312 of the optical fiber cable 310 with the optical video signal transmission port 304 in a predetermined arrangement.

The fiber optic assembly 300 further includes a bracket 320. The bracket 320 is mounted to one or more components of the camera assembly 182 within the handle housing 176. In the illustrative embodiment, the bracket 320 is mounted to the heat transfer plate 400 of the camera assembly 182. The bracket 320 may alternatively or additionally be mounted to the control electronics 305 such as the printed circuit board (PCB) of the camera assembly 182. Referring again to FIG. 5, the fiber module 302 may be sandwiched between the bracket 320 and the heat transfer plate 400, with the heat transfer pad 313, if present, sandwiched between the fiber module 302 and heat transfer plate 400. The heat transfer plate 400 may then be attached to the rotatable bracket 204, 208; that is, the heat transfer plate 400 may be attached to the bracket 204 and/or the bracket 208. In the illustrative embodiment, the fiber module 302 is positioned along the body of the camera 184, that is, disposed laterally to the side of and in spaced relationship relative the camera 184 radially outward from the rotation axis R of the camera 184, and between the camera 184 and the inner perimeter of the handle housing 176. Further, in the illustrative embodiment, the fiber module 302 is not connected to the camera 184 itself but rather to one or more brackets 204, 208 to which the camera 184 also is connected. In some embodiments, the fiber module 302 may be co-located with the control electronics 305 of the camera assembly 182 and/or positioned axially above the camera 184.

The bracket 320 retains the fiber module 302 in a fixed position relative to the camera 184. In the embodiment shown, the bracket 320 retains the fiber module 302 in an orientation such that the optical video signal transmission port 304 is arranged toward the distal end 177 of the handle 176. The bracket 320 also retains the distal end 312 of the optical fiber cable 310 in a fixed position relative to the camera 184 and relative to the fiber module 302 and optical video signal transmission port 304.

With additional reference to FIGS. 9-12, the bracket 320 includes an interface retention portion 322 and a cable retention portion 324. A fastening member 325 is located between and connects or bridges the interface retention portion 322 and the cable retention portion 324.

The cable retention portion 324 of the bracket 320 is configured as a channel 326 including a bottom wall 328 and side walls 330, 332. The channel 326 extends between a proximal end 334 and a distal end 336 along a direction C. The side walls 330, 332 extend in a height direction H from the bottom wall 332. The fastening member 325 is connected to one of the side walls 330 of the channel 326. In the exemplary embodiment shown, the side walls 330, 332 at the proximal end 334 are tapered. In other embodiments, the side walls 330, 332 have a constant height between the proximal end 334 and the distal end 336. The cable retention portion 324 may also be referred to as a guide channel in that it guides the optical fiber cable 310 within the handle housing 176 and toward the light head housing 116, 122.

The interface retention portion 322 of the bracket 320 includes an interface channel 338 including a bottom wall 340 and side walls 342, 344. The interface channel 338 extends between a proximal end 346 and a distal end 348 along a direction B. The side walls 342, 344 extend in a height direction H from the bottom wall 340. A distal wall 350 is located at the distal end 348 of the interface channel 338 and extends between the side walls 342, 344 and in the height direction H. The distal wall 350 is arranged orthogonal to the side walls 342, 344 of the interface channel 338. A slot 352 is provided in the distal wall 350 that provides for fluid communication through the distal wall and into the interface channel 338.

A proximal wall 354 is located at the proximal end 346 of the interface channel 338 and extends between the side walls 342, 344 and in the height direction H. The proximal wall 354 is arranged orthogonal to the side walls 342, 344 of the interface channel 338. A slot 356 is provided in the proximal wall 354 that provides for fluid communication through the proximal wall 354 and into the interface channel 338.

At each end of the proximal wall 354 a fiber module retention channel 358, 360 extends along the height direction H between a proximal end 362, 364 and a distal end 366, 368. Each fiber module retention channel 358, 360 includes a bottom wall 370, 372 and side walls 354, 374, 376, wherein a portion of the distal wall 354 forms a side wall of each of the fiber module retention channels 358, 360.

Retention walls 378, 380 extend from the side walls 374, 376 of each fiber module retention channel 358, 360. The retention walls 378, 380 extend from the side wall 374, 376 at the distal ends 366, 368 of the fiber module retention channels 358, 360. In the illustrative embodiment, each retention wall 378, 380 is oriented parallel to the bottom wall 340 of the interface channel 338.

The fastening member 325 includes an orifice 382 (e.g., a bolt hole) through which a fastener 384 (e.g., screw, rivet, etc.) may be inserted for securing the bracket 320 to another member, such as the heat transfer plate 400 or other component of the camera assembly 182. It will be appreciated that the fastening member 325 may include any suitable coupling mechanism and arrangement to fix the bracket 320 to the camera assembly 182. For example, in some embodiments, the fastening member 325 may include a bolt hole pattern through which fasteners (e.g., screws, rivets, etc.) may be respectively inserted for securing the bracket 320. In other embodiments, the fastening member 325 may have an arrangement of one or more tabs configured to mate with one or more orifices on the camera 184 or other component(s) of the camera assembly 182. In other embodiments, the fastening member 325 may have a surface that may be adhered to a surface of a component of the camera assembly 182 by an adhesive.

In the illustrative embodiment, the interface retention portion 322 and cable retention portion 324 are arranged such that the channel 326 of the cable retention portion 324 and the interface channel 338 of the interface retention portion 322 are parallel to one another in a direction orthogonal to the height direction H. In other embodiments, the interface retention portion 322 and cable retention portion 324 are arranged such that the channel 326 of the cable retention portion 324 and the interface channel 338 of the interface retention portion 322 are arranged non-parallel to one another in a direction orthogonal to the height direction H.

As shown in FIGS. 5 and 6, the bracket 320 may be secured to the camera assembly 182 and may retain the fiber module 302 in optical communication with the distal end 312 of the optical fiber cable 310. With additional reference to FIGS. 13-15, the distal end of the optical fiber cable 310 may be inserted into the tubular member 306 of the fiber module 302. The distal end 312 of the optical fiber cable 310 may be set at a predetermined distance from the output (e.g., lens) of the optical video signal transmission port 304. This distance may be set based on the length of the tubular member 306 and the position of the ferrule 314 on the optical fiber cable 310 relative to the distal end 312 of the optical fiber cable 310. The outer diameter of the ferrule 314 may be larger than the inner diameter of the tubular member 306 such that ferrule 314 contacts the distal end 307 of the tubular member 306 and prevents the optical fiber cable 310 from being inserted any further into the tubular member 306. In some embodiments, the position of the ferrule 314 is on the optical fiber cable 310 is adjustable. The predetermined distance between the distal end 312 of the inserted optical fiber cable 310 and the output (e.g., lens) of the optical video signal transmission port 304 may be any suitable distance. In some embodiments, the distance ranges from 0.1 mm to 1 cm. In other embodiments, the distance is less than 0.1 mm. It will also be appreciated that in some embodiments, the distal end 312 of the inserted optical fiber cable 310 may be in contact with the output of the optical video signal transmission port 304 such that the distance is zero mm.

The tubular member 306 defines an aperture at which the ferrule 314 seats to align the distal end 312 of the optical fiber cable 310 with an optical video signal transmission port 304 of the fiber module 302. In some embodiments, the ferrule 314 seats at the distal end 307 of the tubular member 306 to laterally align the optical fiber cable 310 with an axis of the optical video signal transmission port 304 of the fiber module 302. In other embodiments, the ferrule 314 seats at the tubular member 306 to angularly align the optical fiber cable 310 with an axis of the optical video signal transmission port 304 of the fiber module 302.

The fiber module 302 includes a flange 309 that slidably fits into the fiber module retention channels 358, 360. With the flange 309 inserted in the fiber module retention channels 358, 360, the fiber module 302 is restricted in movement in a direction along the direction B of the interface channel. The flange 309 of the fiber module 302 is inserted into the fiber module retention channels 358, 360 from a direction proximate the open top surface of the channel, and the retention walls 378, 380 prevent the fiber module 302 from extending past a predetermined position along the height direction H.

A biasing member 316 is provided on the optical fiber cable 310 at a side of the ferrule 314 opposite the distal end 312 of the optical fiber cable 310. In the exemplary embodiment shown, the biasing member 316 is a spring 316. In other exemplary embodiments, the biasing member 316 is a compressible, resilient material such as a rubber, foam, and the like. When the fiber module 302 and optical fiber cable 310 are inserted into the interface retention portion 322 of the bracket 320, one end of the biasing member 316 is in contact with the ferrule 314 and the other end of the biasing member 316 is in contact with the distal wall 350. The biasing member 316 provides a continuous biasing force against the ferrule 314 to retain the ferrule 314 against the distal end 317 of the tubular member 306, thereby retaining the distal end 312 of the optical fiber cable 310 in the predetermined position relative to the output (e.g., lens) of the optical video signal transmission port 304 of the fiber module 302.

In some embodiments, a sheath 315 may be provided around the optical fiber cable 310 proximate the distal end 312 of the optical fiber cable 310. In the embodiment shown, the ferrule 314 and biasing member 316 are disposed between the distal end 312 of the optical fiber cable 310 and the sheath 315. The sheath 315 may also pass through the slot 352 in the distal wall 350. The sheath 350 may provide a stiffness that inhibits or prevents the optical fiber cable 310 from bending or increases the optical fiber cable's resistance to bending proximate the distal wall 350.

When secured to the camera assembly 182, the retention walls 378, 380 hold the fiber module 302 against the camera assembly 182; and the distal wall 350, proximal wall 354, and/or bottom surface 340 of the interface channel and bottom surface of the interface channel hold the distal end 312 of the optical fiber cable 310 against the camera assembly 182.

Figure 13:
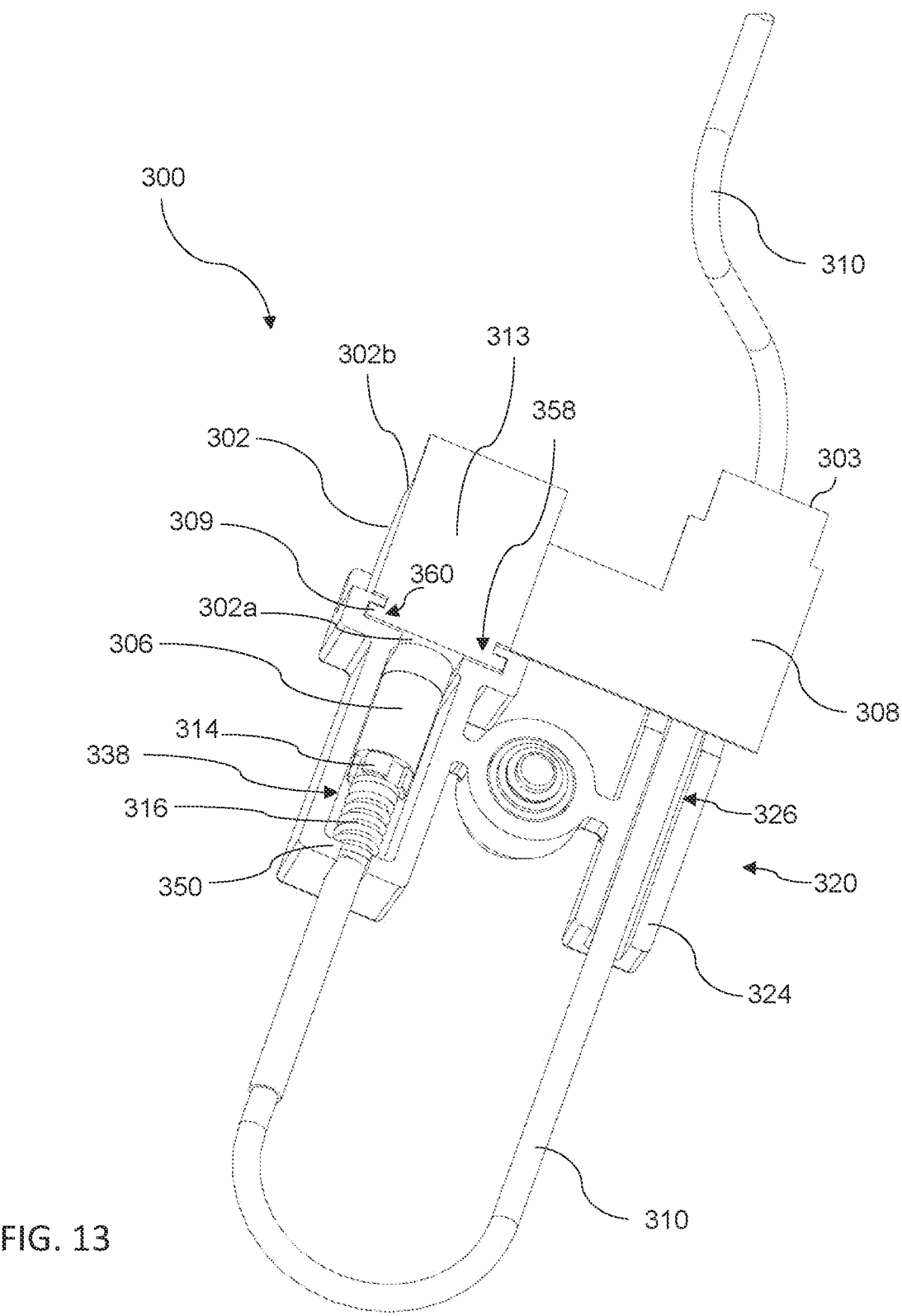
FIG. 13 is a rear perspective view showing the bracket of FIG. 9 and parts of a fiber optic assembly.
Figure 14:
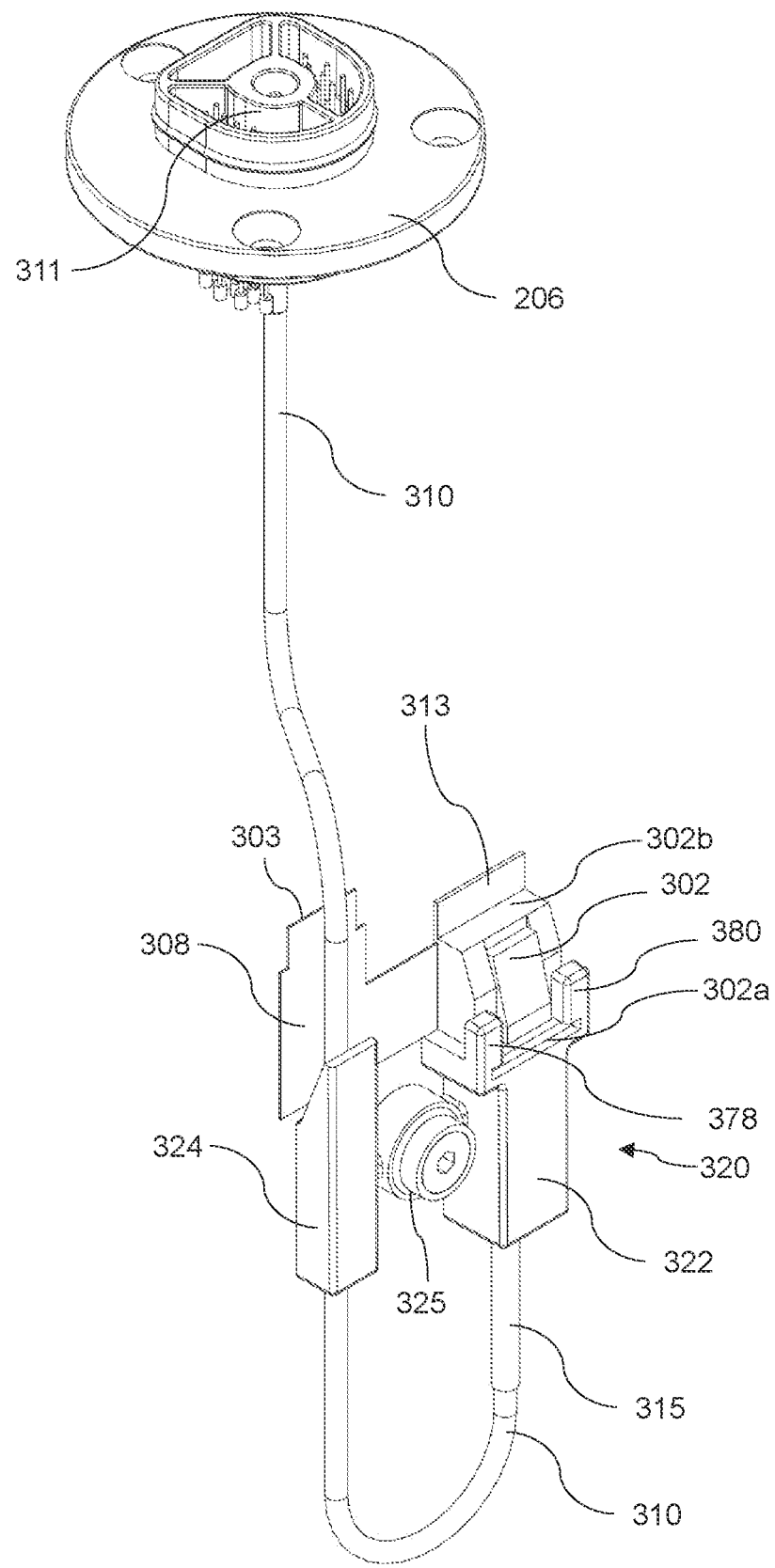
FIG. 14 is a front perspective view showing the bracket of FIG. 9 and parts of a fiber optic assembly and handle.
Figure 15:
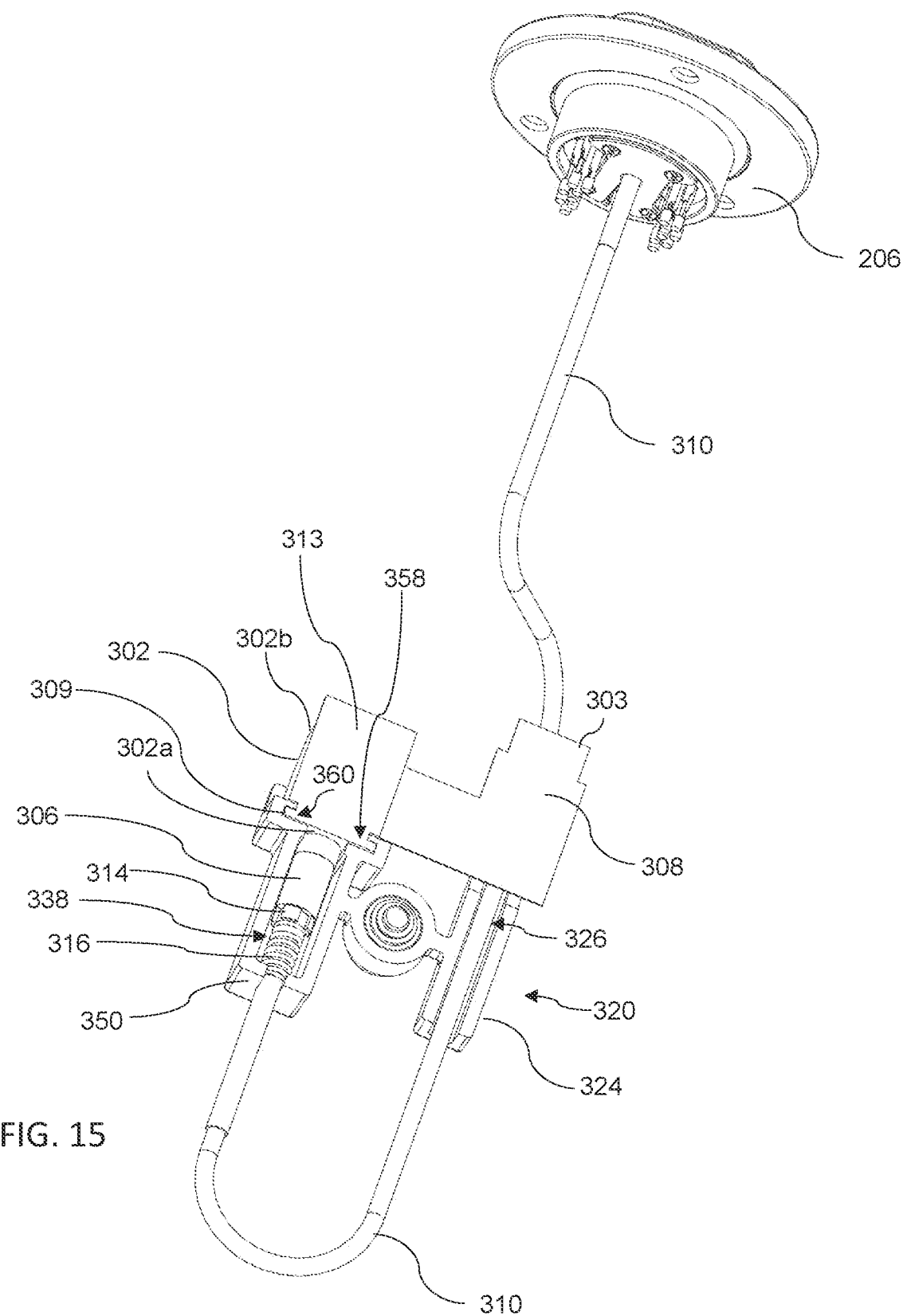
FIG. 15 is a rear perspective view showing the bracket and parts of the fiber optic assembly and handle.
Figure 16:
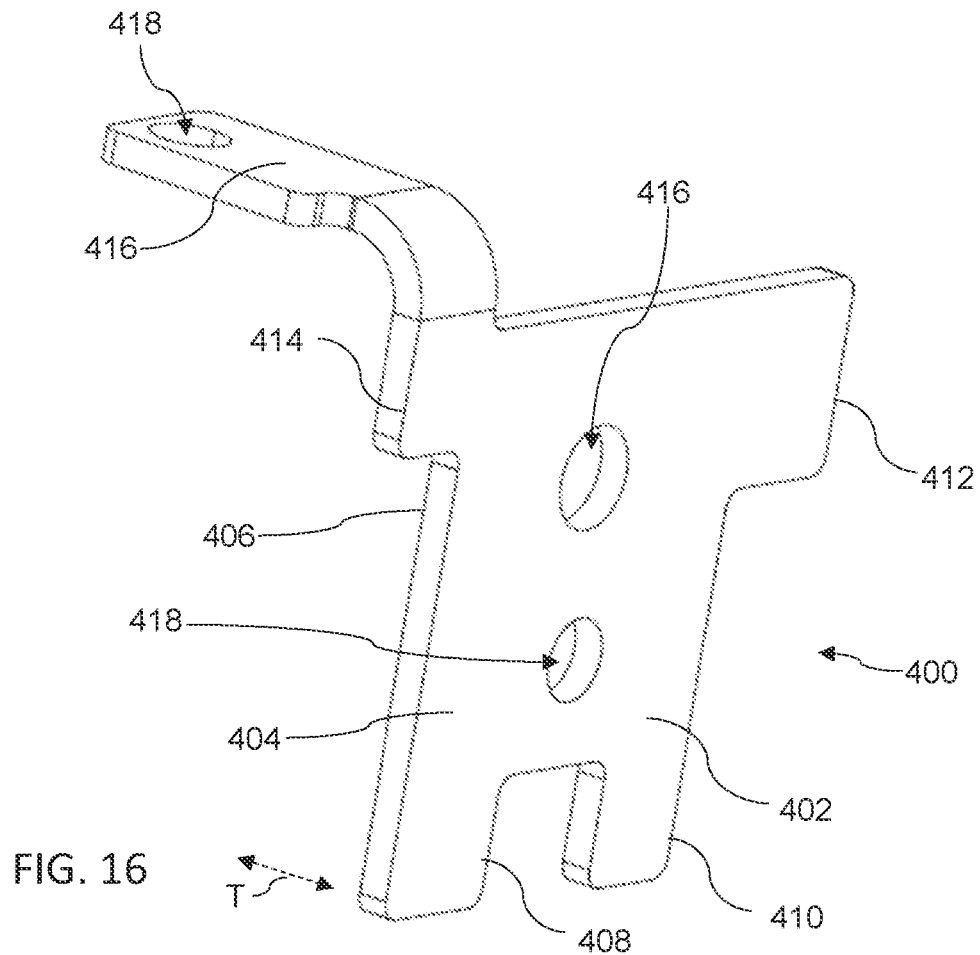
FIG. 16 is a front perspective view of a heat transfer plate in accordance with an embodiment of the present disclosure.
Figure 17:
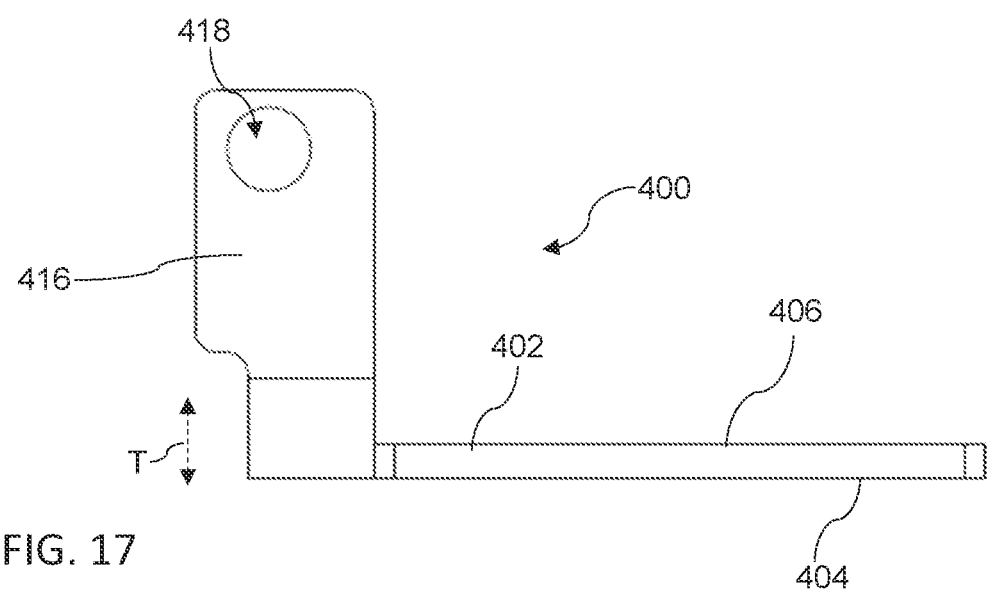
FIG. 17 is a top view of the heat transfer plate of FIG. 16.
Figure 18:
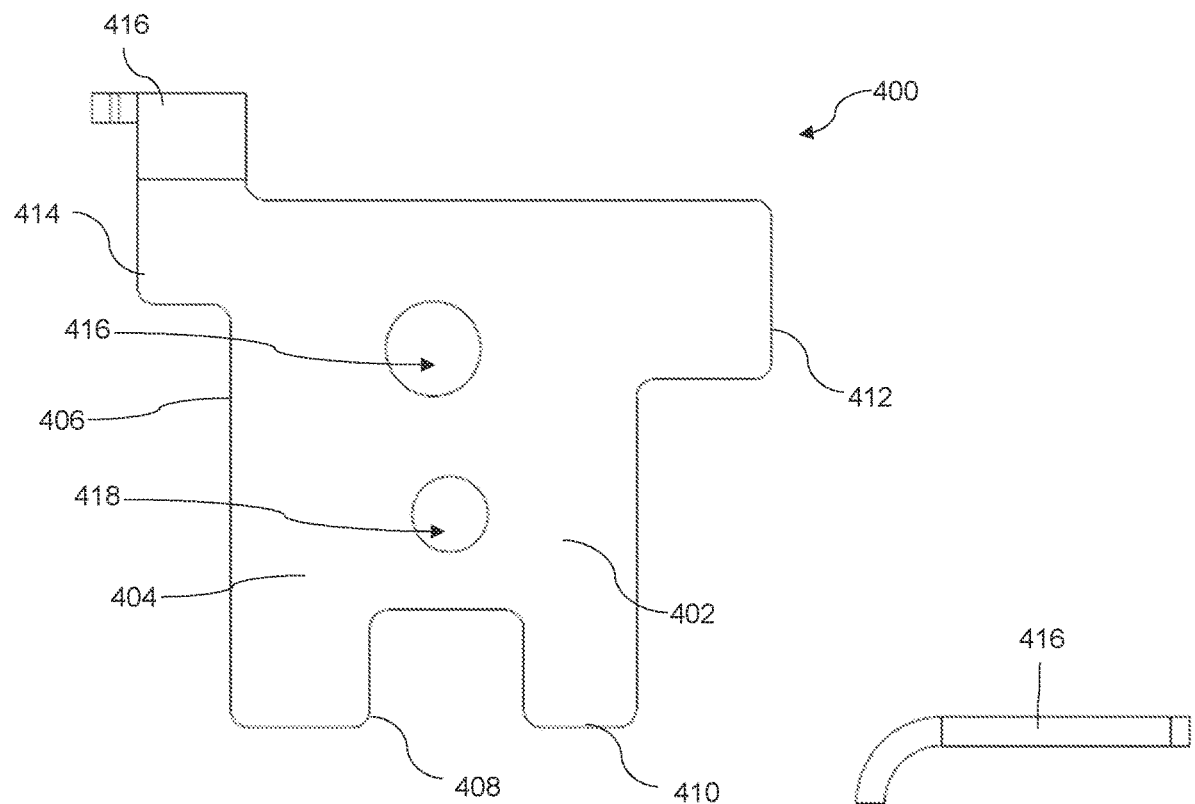
FIG. 18 is a front elevation view of the heat transfer plate of FIG. 16.
Figure 19:
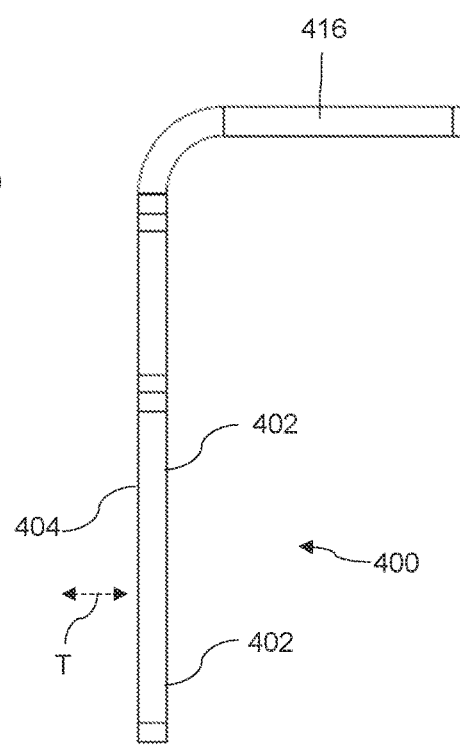
FIG. 19 is a side elevation view of the heat transfer plate of FIG. 16.
Figure 20:
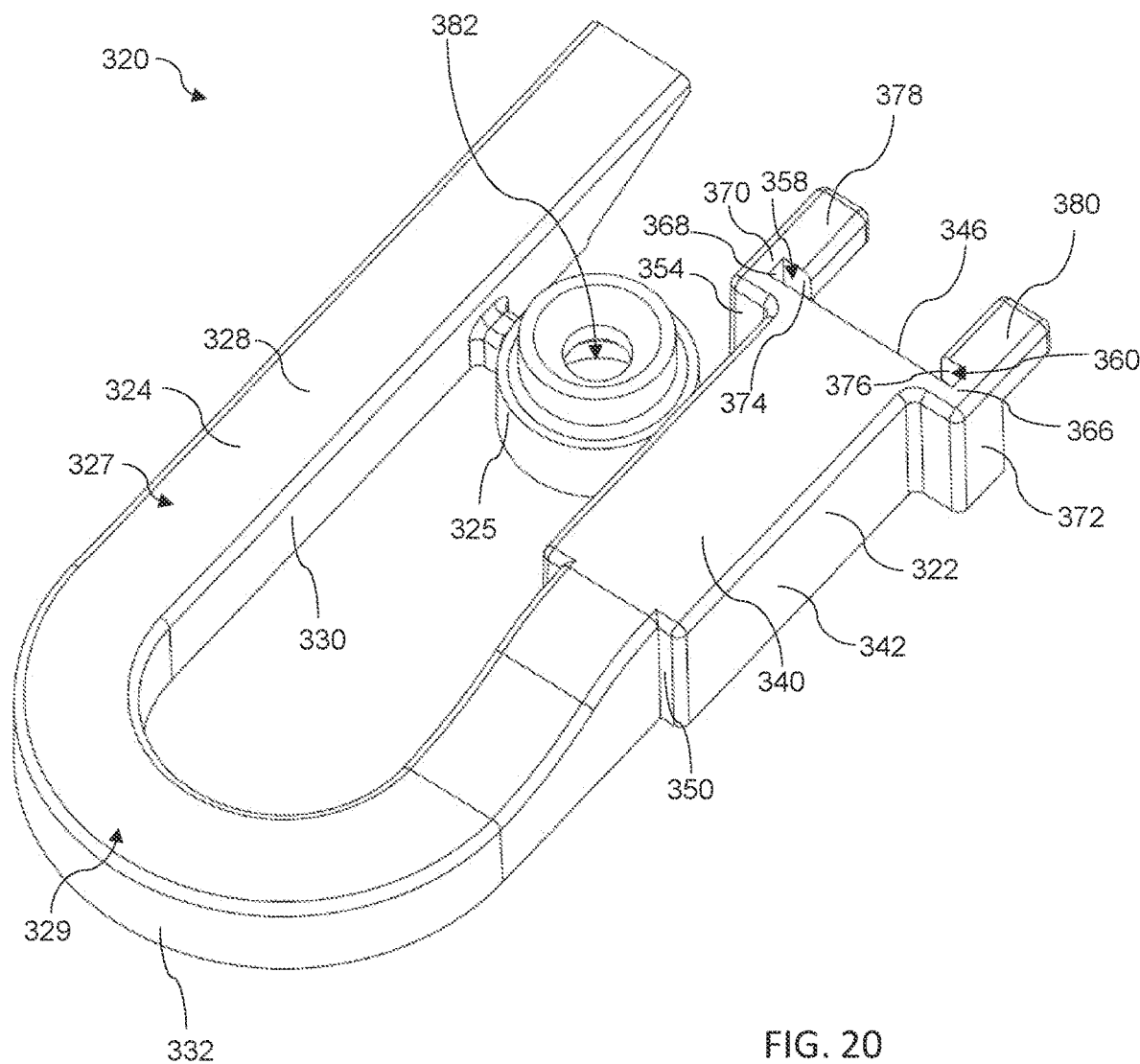
FIG. 20 is a front perspective view of a bracket in accordance with another embodiment of the present disclosure.
Figure 21:
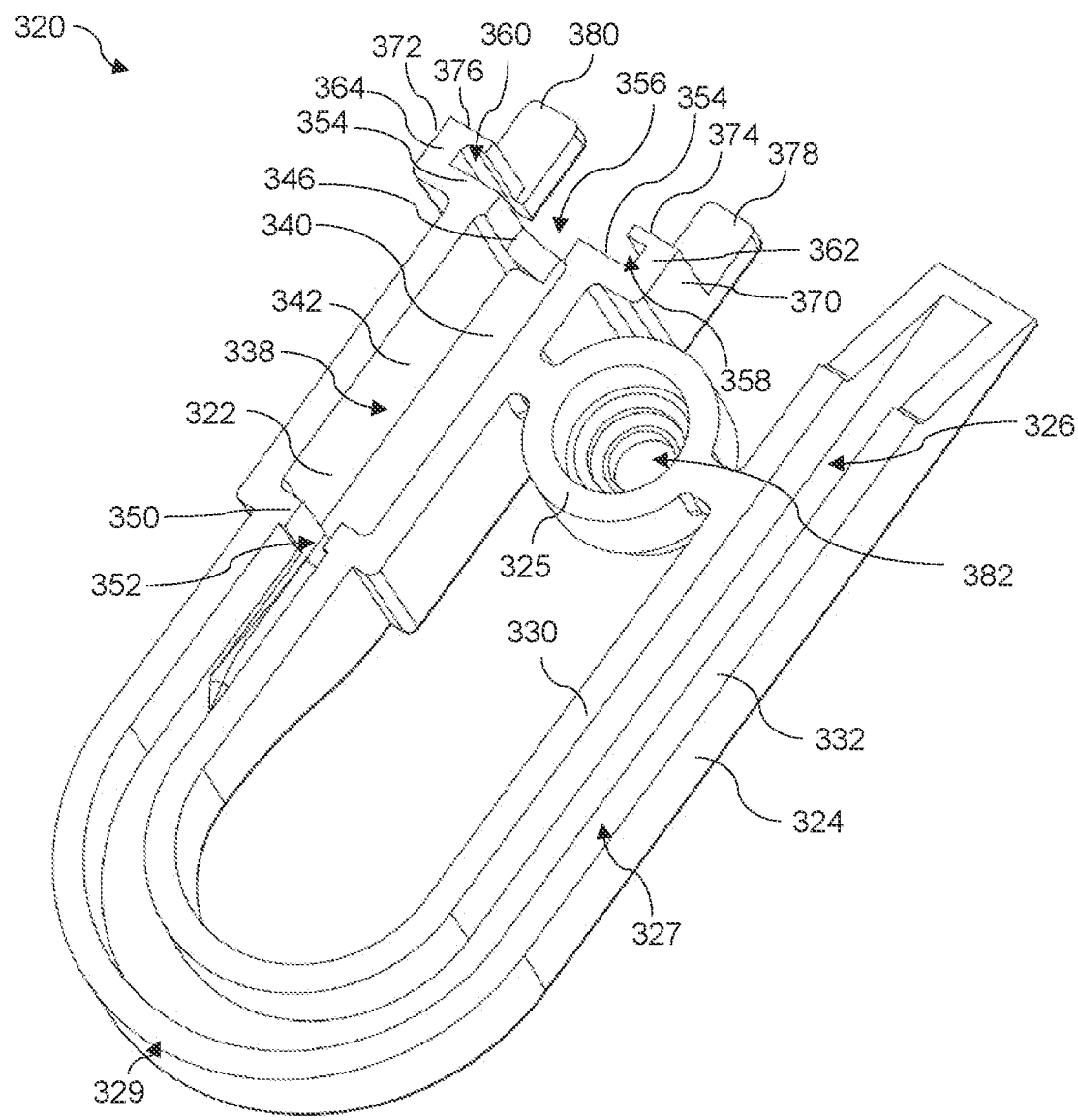
FIG. 21 is a rear perspective view of the bracket of FIG. 20.
Figure 26:
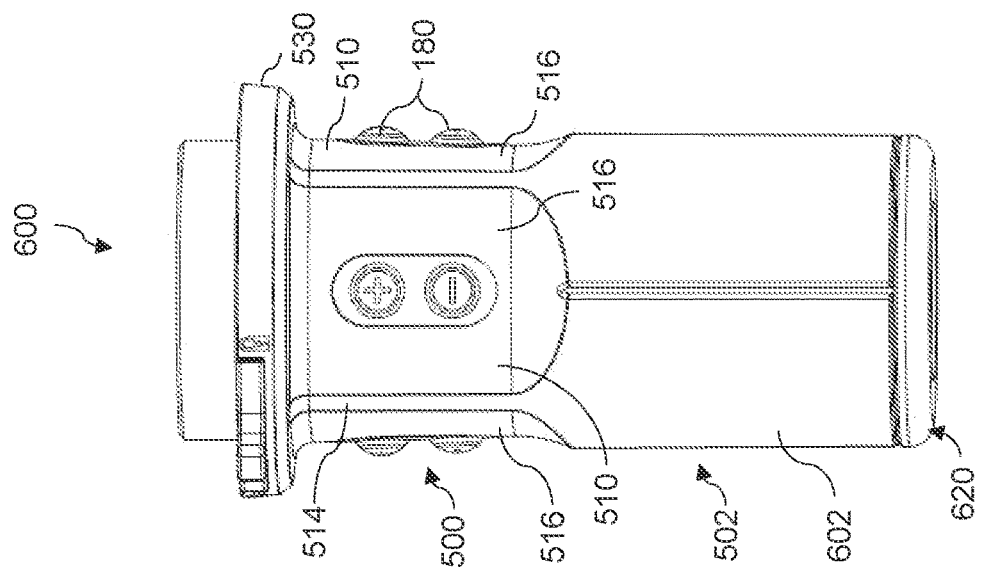
FIG. 26 is a front elevation view of the FIG. 24 handle, as viewed from the front of FIG. 24 and showing buttons in the plane of the paper.
Figure 25:
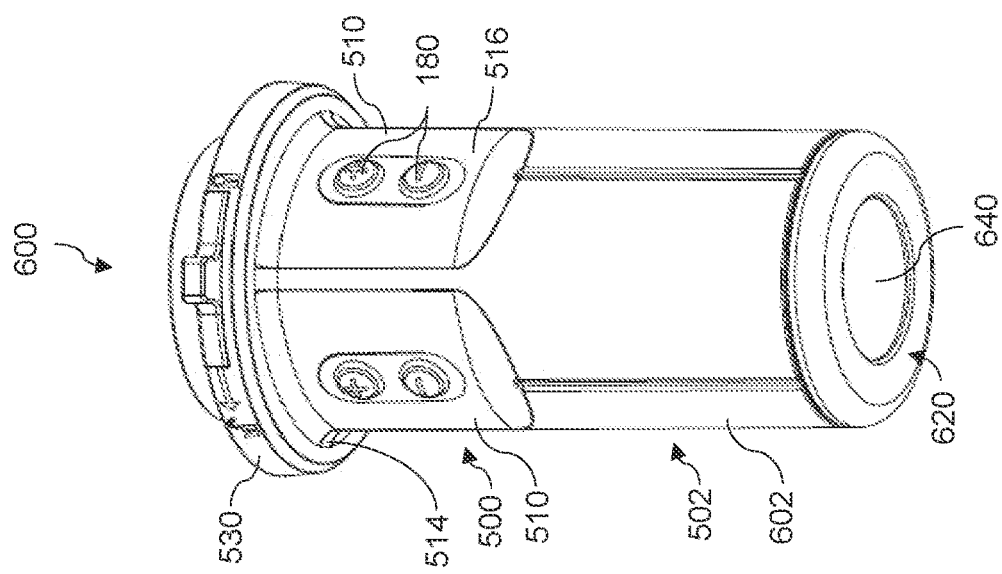
FIG. 25 is a bottom perspective view of the FIG. 24 handle.
Figure 24:
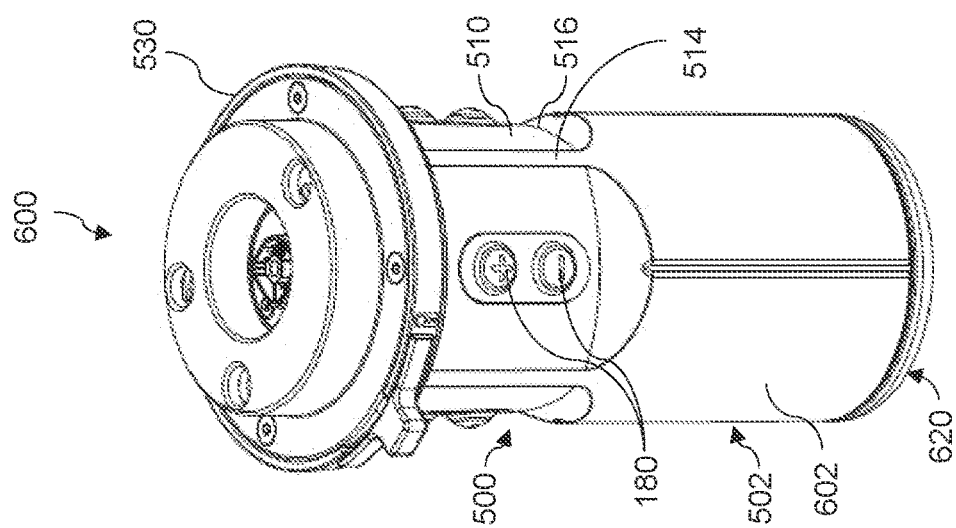
FIG. 24 is a top perspective view of a handle in accordance with another embodiment of the present disclosure having a handle housing including a grip portion.
Figure 29:
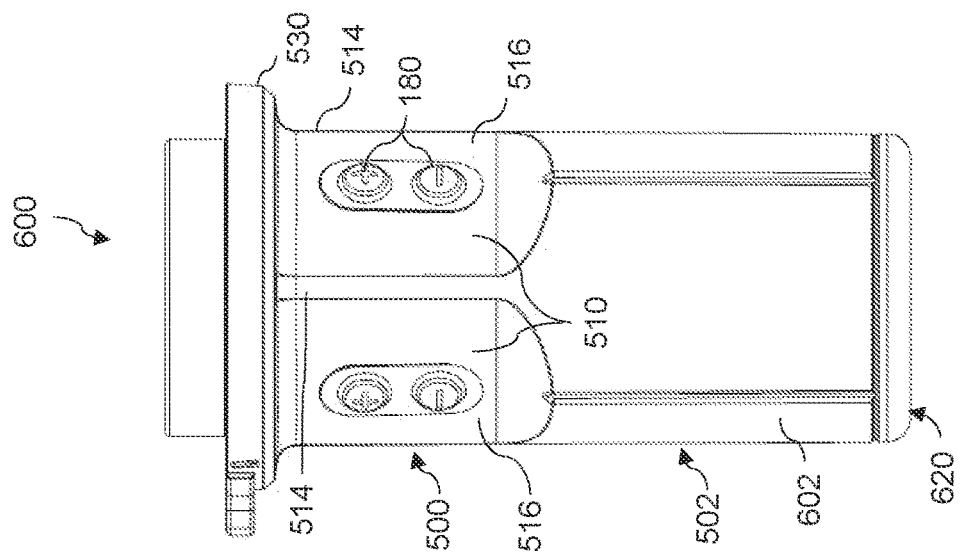
FIG. 29 is a side elevation view of the FIG. 24 handle, as viewed from the right of FIG. 25.
Figure 28:
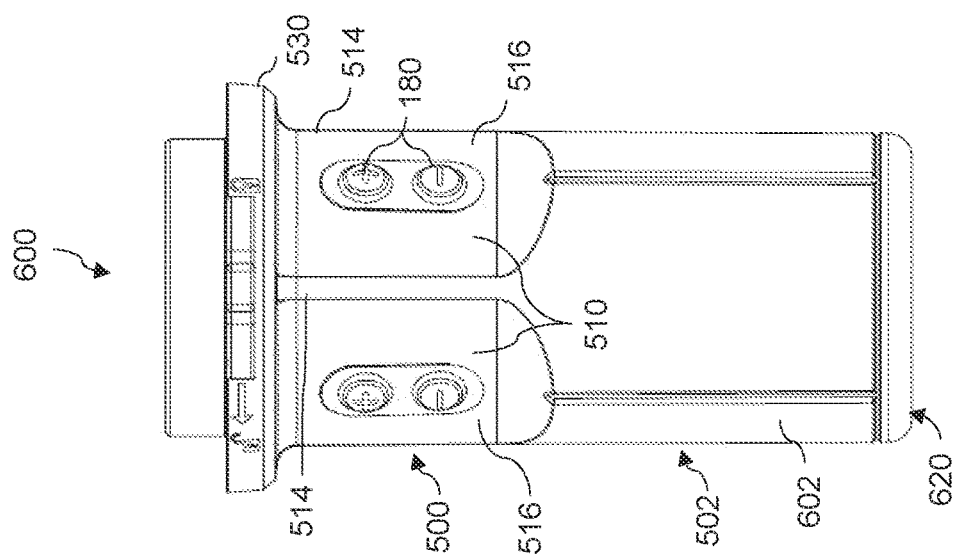
FIG. 28 is a side elevation view of the FIG. 24 handle, as viewed from the front of FIG. 25.
Figure 27:
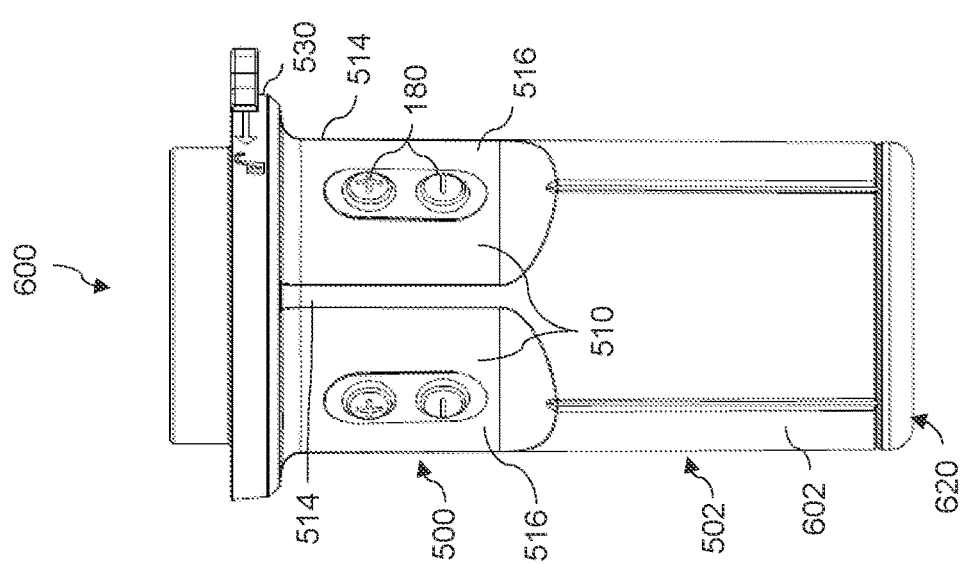
FIG. 27 is a side elevation view of the FIG. 24 handle, as viewed from the left of FIG. 25.
Figure 31:
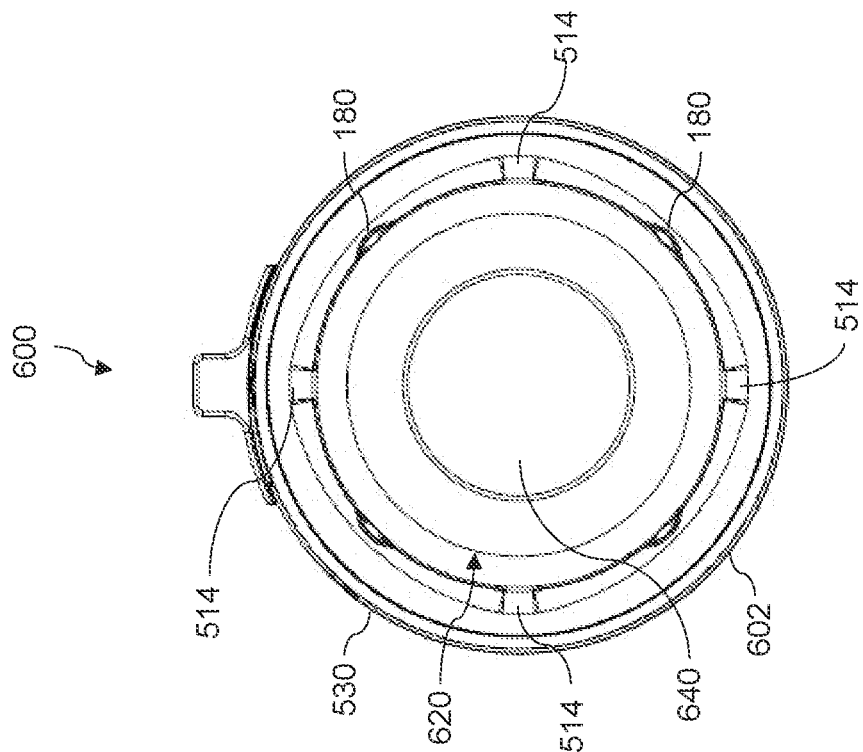
FIG. 31 is a bottom plan view of the FIG. 24 handle.
Figure 30:
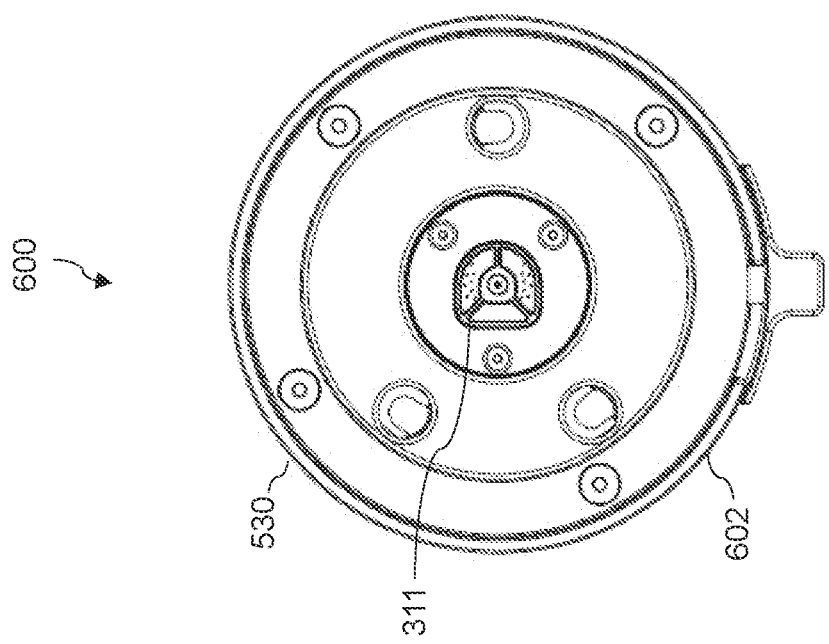
FIG. 30 is a top plan view of the FIG. 24 handle.
Figure 33:
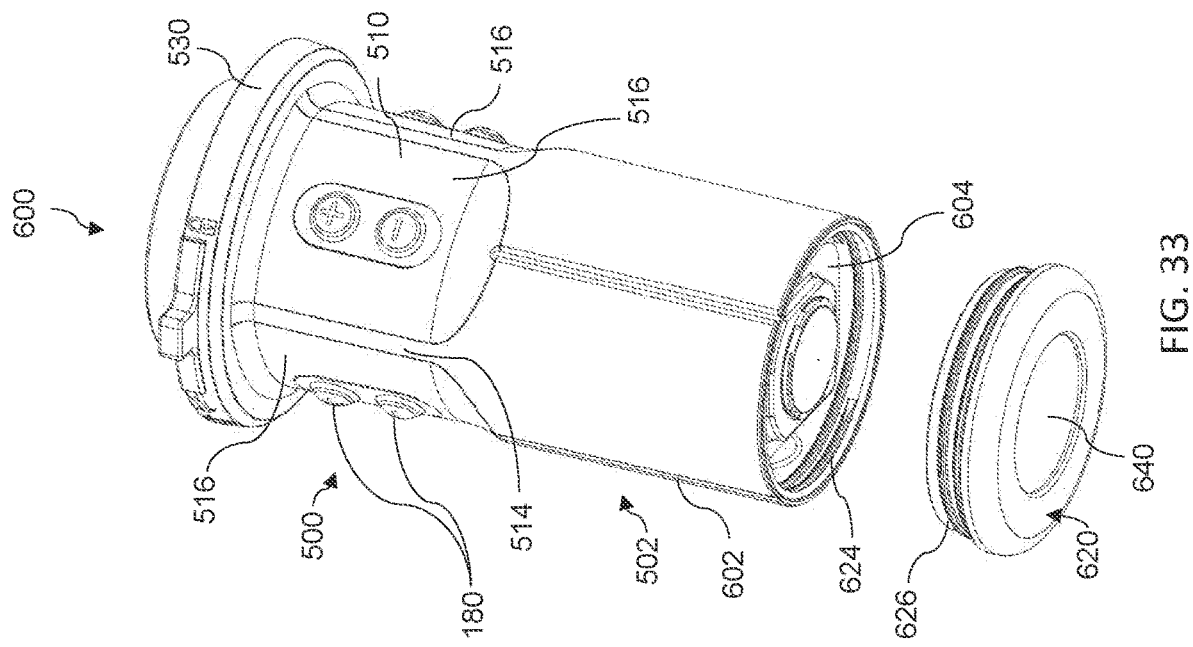
FIG. 33 is similar to FIG. 32 except exploded to show a cap of the handle removed.
Figure 32:
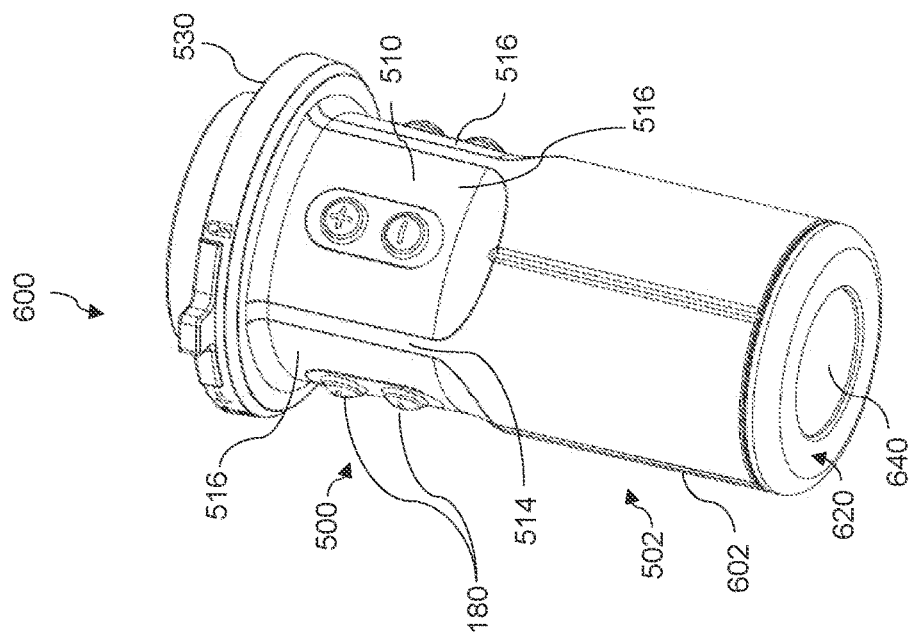
FIG. 32 is a bottom perspective view of the FIG. 24 handle.
Figure 36:
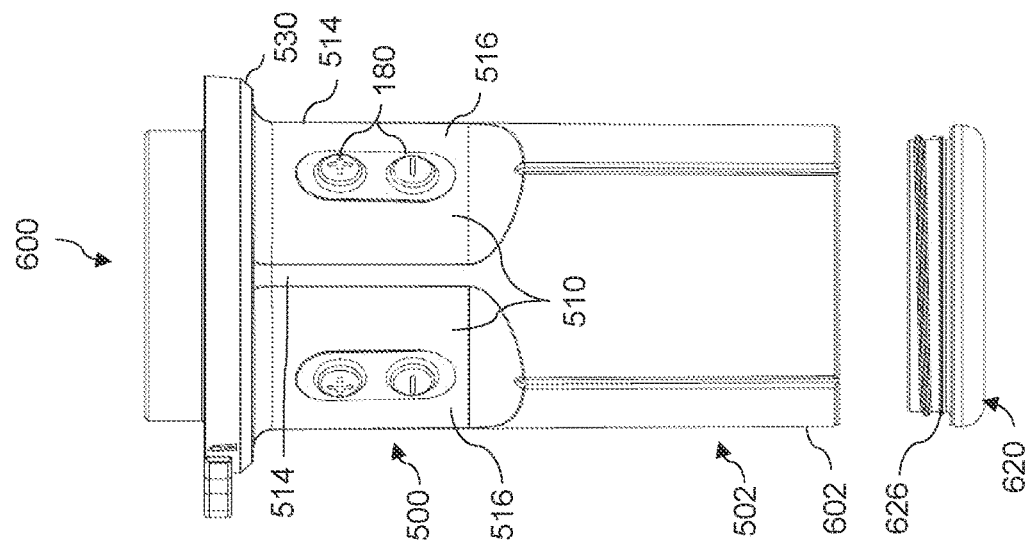
FIG. 36 is similar to FIG. 29 except exploded to show a cap of the handle removed.
Figure 35:
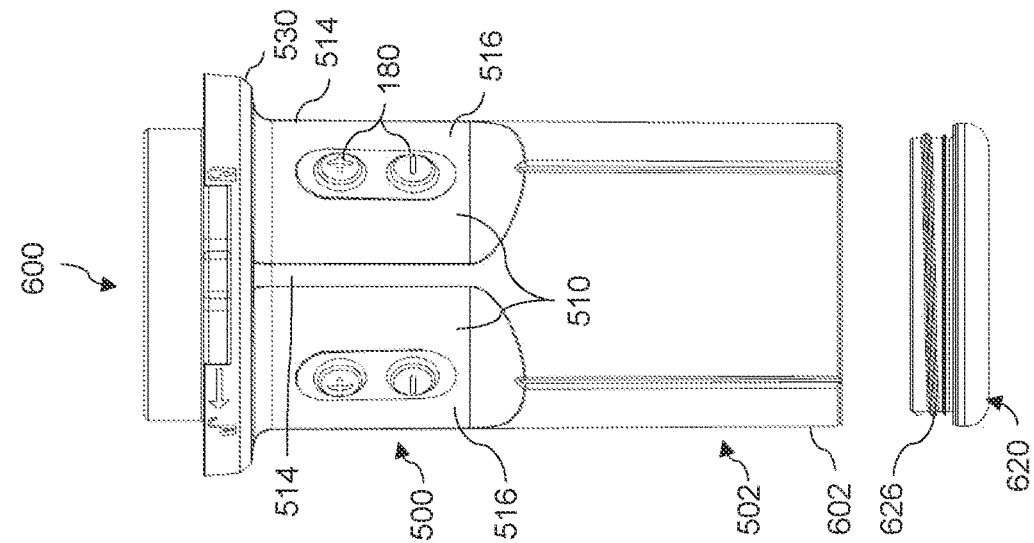
FIG. 35 is similar to FIG. 28 except exploded to show a cap of the handle removed.
Figure 34:
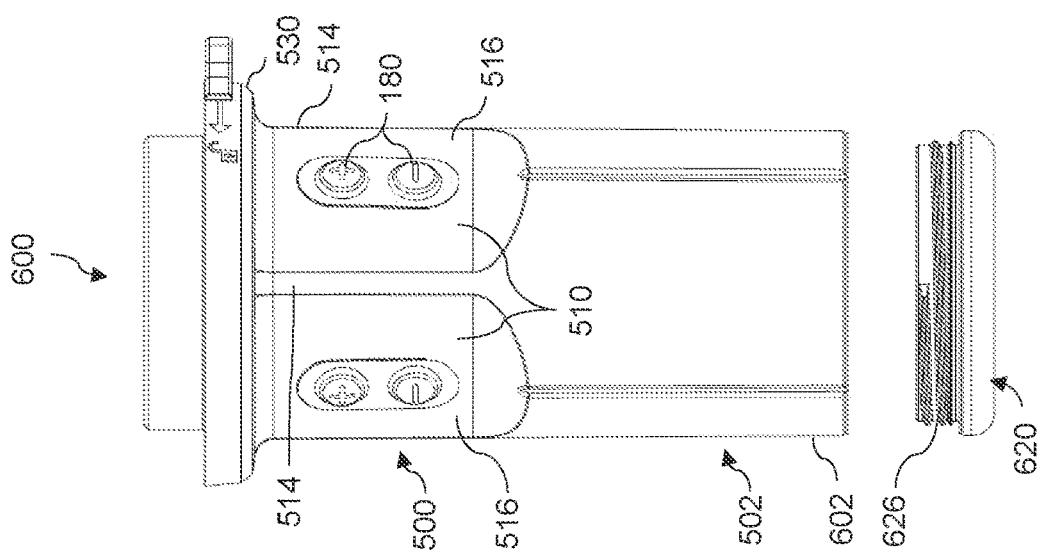
FIG. 34 is similar to FIG. 27 except exploded to show a cap of the handle removed.

With continued reference to FIGS. 13-15, the optical fiber cable 310 is routed through the distal wall of the interface retention portion, is curved, and is routed through the cable retention portion 324 of the bracket 320. The curvature of the optical fiber cable 310 has a radius of curvature (bend radius) that allows for the optical signal to propagate in the optical fiber without or with an acceptable minimum loss of the signal. In some embodiments, the radius of curvature is 1 cm to 4 cm. A suitable optical fiber cable 310 may be, for example, a multimode (MM) 50 micron OM4 bend insensitive fiber. In some embodiments, the optical fiber cable 310 may be a single mode (SM) fiber, or a multimode (MM) fiber of 62.5 micron diameter. In still other embodiments, it is contemplated that the optical fiber cable 310 may comprise an OM5 or OM6 designated fiber.

The cable retention portion 324 and the interface retention portion 322 are separated from one another by a predetermined distance so as to set a radius of curvature of the optical fiber cable 310 that allows for transmission of the optical video signal. In some embodiments, the distance between the channel 326 of the cable retention portion 324 and the channel 338 of the interface retention portion 322 is 2 cm to 8 cm. In some embodiments, the optical fiber cable 310 is fixed in the channel 326 of the cable retention portion 324. The diameter of the optical fiber cable 310 relative to the channel 326 may be such that the optical fiber cable 310 is prevented from freely moving through the channel 326 due to frictional forces between the optical fiber cable 310 and the channel 326. In other embodiments, the optical fiber cable 310 is freely movable within the channel 326.

The optical fiber cable 310 is routed through the cable retention portion 324 of the bracket 320 and to the light head housing 116, 122. The optical fiber cable 310 may be routed in any suitable manner between the bracket 320 and the light head housing 116, 122, so long as an acceptable bend radius of the optical fiber cable 310 is maintained. In the exemplary embodiment shown the cable retention portion 324 of the bracket 320 retains the optical fiber cable 310 while also allowing slack in the optical fiber cable 310 between the cable retention portion 324 and the light head housing 116, 122. In some embodiments, the slack in the optical fiber cable 310 may allow for flexibility in the optical fiber cable 310 during rotation of the camera assembly 182 so that, for example, the optical fiber cable 310 merely bends and flexes as needed between the cable retention portion 324 and for example the accessory port connector 311 in the light head housing 116, 122, as shown in FIGS. 4-6, 14 and 15. The optical fiber cable 310 is curved with a suitable bend radius and routed through the spindle 206 and to the light head housing 116, 122. The optical fiber cable 310 and/or any additional or alternate cables may be routed in any suitable manner through the components of the medical device support system 100 to reach for example the display 202 or other components of the system 100.

Thus, the distal end 312 of the optical fiber cable 310 includes the ferrule 314 and the bracket 320 includes the interface channel 338 within which the ferrule 314 seats to align the distal end 312 of the optical fiber cable 310 with the optical video signal transmission port 304 of the fiber module 302. Further, the bracket 320 includes the biasing member 316 that exerts a continuous force against the ferrule 314 to compress the distal end 312 of the optical fiber cable 310 against the optical video signal transmission port 304 of the fiber module 302. The interface channel 338 has at its opposite ends the distal wall 350 and the fiber module 302 respectively, and, as shown in FIG. 13, the biasing member 316 has a first end that exerts the continuous force against the ferrule 314 and a second end that abuts the distal wall 350. The bracket 320 includes the guide channel 326 that guides the optical fiber cable 310 within the handle housing 176 and to the light head housing 116, 122. The optical fiber cable 310 has a bend radius as it passes between the distal wall 350 and the light head housing 116, 122.

With continued reference to FIG. 5, and with additional reference to FIGS. 16-19, the camera assembly 182 may include a heat transfer plate 400. In the example shown, the bracket 320 may be fixed to the camera assembly 182 such that the bracket 320 and the fiber module 302 are in contact with the heat transfer plate 400. The heat transfer plate 400 may be made from metal or any other suitable heat transfer material. The heat transfer plate 400 is in heat transmissive contact with the fiber module 302 to draw heat away from the fiber module 302.

FIGS. 16-19 show that the heat transfer plate 400 includes a main body 402 having major surfaces 404, 406 spaced apart from one another in a thickness direction T. The main body 402 is shown as having planar major surfaces 404, 406, although it will be appreciated that in other embodiments, the main body 402 (and the major surfaces thereof) may be curved in one or more directions. The perimeter of the main body 402 (viewed in a direction normal to the major surfaces, such as that shown in FIG. 18) may have any suitable shape. In the illustrated embodiment, the main body 402 has a perimeter including protrusions 408, 410, 412, 414 such that the profile of the major surfaces allow for the bracket 320 to at least partially correspond to the perimeter of the bracket 320, as well as the fiber module 302 when mounted to the bracket 320. This may allow for increased contact between the bracket 320 and the heat transfer plate 400, as well as the fiber module 302 and the heat transfer plate 400. The main body 402 of the heat transfer plate 400 includes one or more orifices 418, which may allow for the heat transfer plate 400 to be mounted (e.g., via a fastener such as a screw, rivet, etc.) to the camera assembly 182 and/or may allow for the bracket 320 to be mounted (e.g., via a fastener such as a screw, rivet, etc.) to the heat transfer plate 400.

In some embodiments, the heat transfer plate 400 may be coupled to a heat sink to provide further dissipation of heat from the fiber module 302. In the embodiment shown, the heat transfer plate 400 includes a tab 416 that is arranged orthogonal to the main body 402 of the heat transfer plate 400. The tab 416 includes an orifice 418 through which the tab 416 may be secured (e.g., via a fastener such as a screw, rivet, etc.) to a separate heat sink in the camera assembly 182.

FIGS. 20-23 show another exemplary embodiment of the bracket 320. In this embodiment, the interface retention portion 322 and the fastening portion 325 are similar to that described above with respect to the bracket 320 shown in FIGS. 9-15, and the features thereof will not be repeated for the sake of brevity. However, the cable retention portion 324 includes a channel 326 that is in contact with the distal wall 348 of the interface retention portion 322. As shown, the channel 326 includes a bottom wall 328 and side walls 330, 332, and the channel 326 includes a linear portion 327 and a curved portion 329. The curved portion of the channel has a predetermined radius of curvature (bend radius) and serves a guide for setting and maintaining the radius of curvature of the optical fiber cable 310. It will be appreciated that the bracket shown in FIGS. 20-23 may be implemented in any of the embodiments of the handle shown and described in the present disclosure.

Referring again to FIGS. 3 and 4, the handle 164 of the light head 110 will now be described in greater detail. The handle 164 includes a handle housing 176 that has an upper generally tubular section 500 mounted to the light head housing 116, 122 and a lower generally tubular section 502 extending downward from a bottom of the upper generally tubular section 500. As shown in FIGS. 3 and 4, the outer perimeter of the lower generally tubular section 502 is relatively wider in axial cross section than the outer perimeter of the upper generally tubular section 500 over a portion, for example a plurality of recesses 510, of the upper generally tubular section 500. With particular reference to FIG. 4, the width at the axial cross section is perpendicularly across the center axis of the handle housing 176, which in the illustrative embodiment coincides with the afore described rotation axis R. As shown in FIG. 4, the width in axial cross section of the lower generally tubular section 502 is greater than the width in axial cross section of the upper generally tubular section 500 over the portion where the plurality of recesses 510 are provided in the upper generally tubular section 500.

The lower generally tubular section 502 may be cylindrical in shape, as shown, or non-cylindrical in shape. The upper generally tubular section 500 may be generally square tubular in shape, as shown, or non-generally square tubular in shape. The generally square tubular shape of the upper generally tubular section 500 includes the four curved recesses 510 forming the four sides of the square shape and four relatively smaller size curved corners 514 disposed between respective adjacent recesses 510. In other words, the upper generally tubular section 500 has recesses 510 and curved corners 514 disposed in alternate fashion around the outer perimeter of the upper generally tubular section 500, that is, disposed about the center axis (rotation axis R) of the handle housing 176. As will be appreciated, the shape of the upper generally tubular section 500 need not be limited to a generally square shape and the quantity of recesses 510 need not be limited to four. Other embodiments are contemplated. The upper generally tubular section 500 may have any polygonal shape in axial cross section, for example three, five, or six recesses 510, in which case, the upper generally tubular section 500 would have, respectively, a generally triangular tubular shape, a generally pentagonal tubular shape, or a generally hexagonal tubular shape.

The upper generally tubular section 500 and lower generally tubular section 502 may be made of a single monolithic structure, as shown, or a multi-piece construction. The single monolithic structure may be formed by a net shape manufacturing technique or near net shape manufacturing technique, and may include, for example, an injection molded structure or a 3D printed structure. The upper generally tubular section 500 may include a flange 530 that protrudes radially outwardly relative to the recesses 510 and curved corners 514. The flange 530 may cover, for example, mounting structure of the handle 164 and/or mounting structure of the light head housing 116, 122 to which the handle 164 is mounted. In the illustrated embodiment, the width in axial cross section of the lower generally tubular section 502 where the lower generally tubular section 502 transitions to the upper generally tubular section 500 is equal to the width in axial cross section of the upper generally tubular section 500 at the curved corners 514.

As shown in FIG. 3, each recess 510 includes a surface 516 recessed radially inwardly relative to the outer perimeter of the lower generally tubular section 502 and recessed radially inwardly relative to the curved corners 514 of the upper generally tubular section 500. The surfaces 516 may be curved, as shown, or planar (the secant of a circle defined at the radius of the curved corners 514), it being understood that a curved recess generally will provide more capacity inside the handle housing 176 than a planar recess.

The outer perimeter of the handle housing 176 tapers downwardly from the upper most portion of the upper generally tubular section 500 to the lower most portion of the lower generally tubular section 502. In some embodiments, the upper generally tubular section 500 may taper downwardly without the lower generally tubular section 502 doing so, or the lower generally tubular section 502 may taper downwardly without the upper generally tubular section 500 doing so. In still other embodiments, the outer perimeter of the handle housing 176 may not include a taper.

The upper generally tubular section 500 includes the afore described buttons 180. As described above, the buttons 180 may be configured to control attributes of the emitted light from the light head 110, or to interface with a drive motor to rotate the afore mentioned camera assembly 182 within the handle housing 176. The buttons 180 are positioned in the recesses 510 of the upper generally tubular section 500 and, as shown in FIG. 4, protrude radially outwardly from the surfaces 516 of the recesses 510. The amount of protrusion from the surfaces 516 is such that the tops or radially outermost portions of the buttons 180 extend radially outwardly relative to the radial extent in axial cross section of the outer perimeter of the lower generally tubular section 502, or alternately extend radially outwardly approximately to the same radial extent as the outer perimeter of the lower generally tubular section 502. This provides an ergonomic reach to the buttons 180, for example by the thumb of the user's hand, while enabling the user to maintain a grip on the lower generally tubular section 502 by the other digits and palm of the user's hand.

As will be appreciated, the handle 164 allows the camera 184 and other components of the camera assembly 182 to be integrated within the handle 164 while maintaining an ergonomic grip and ergonomic button 180 operation. The inventors have found that commonly available cameras, for example HD, 4K or 8K block cameras, may be so large in size that incorporating such cameras into a surgical light head handle creates incompatibilities with maintaining the handle's ergonomics. The handle 164 including the upper generally tubular section 500 where the buttons 180 are positioned, and the relatively wider lower generally tubular section 502 within which the camera 184 is disposed, solves this problem by enabling incorporation of such a camera while maintaining the handle 164 ergonomic grip and ergonomic button 180 operation. The handle 164 advantageously provides an ergonomic shape and ergonomic size handle housing 176 while incorporating a suitable camera 184 within the handle housing 176.

Referring now to FIGS. 24-38 there is shown a handle 600 in accordance with another embodiment of the invention. The handle 600 is in many respects similar to the above-referenced handle 164 shown in FIGS. 3 and 4, and consequently the same reference numerals are used in FIGS. 24-38 to denote structures corresponding to similar structures in the handle 164. In addition, the foregoing description of the handle 164 is equally applicable to the handle 600 and the following description of the handle 600 is equally applicable to the handle 164, except where differences are noted herein. Moreover, it will be appreciated upon reading and understanding the specification that aspects of the handles 164, 600 may be substituted for one another or used in conjunction with one another where applicable.

As shown in FIGS. 33-36 and 38, the bottom of the lower generally tubular section 502 is open downward. A camera 604 is sized for insertion through the open bottom of the lower generally tubular section 502 to within a handle housing 602 of the handle 600 and axially above the open bottom of the lower generally tubular section 502. The handle housing 602 of the FIGS. 24-38 embodiment differs from the handle housing 176 of the FIGS. 3 and 4 embodiment in that, as shown in FIG. 38, the inner perimeter of the lower generally tubular section 502 is relatively wider in axial cross section than the inner perimeter of the upper generally tubular section 500 whereas in the FIGS. 3 and 4 embodiment the inner perimeter of the lower generally tubular section 502 has approximately the same width in axial cross section as the inner perimeter of the upper generally tubular section 500, assuming a negligible effect in the taper of the handle housing 176 and handle housing 602. This is accomplished in the illustrative embodiment by a shoulder 606 that transitions radially outwardly from the inner perimeter of the upper generally tubular section 500 to the inner perimeter of the lower generally tubular section 502.

As will be appreciated, the relatively wider inner perimeter of the lower generally tubular section 502 of the handle housing 602 enables the handle housing 602 to accommodate a wider camera 604, that is, a camera 604 that is relatively wider in axial cross section than the width of the inner perimeter of the upper generally tubular section 500 yet relatively narrower in axial cross section than the width of the inner perimeter of the lower generally tubular section 502. As shown in FIG. 38, the camera 604 is relatively wider in axial cross section than the width of the inner perimeter of the upper generally tubular section 500 yet still fits within the inner perimeter of the lower generally tubular section 502. Thus, the camera 604 is configured to be inserted into and contained within the inner perimeter of the lower generally tubular section 502 but not into or within the inner perimeter of the upper generally tubular section 500. This is regardless of the position of the camera 604 about the center axis of the handle housing 602. At least one axial cross section across the width of the camera 604, that is perpendicularly across the center axis of the handle housing 602, is relatively wider than any width in axial cross section across the width of the inner perimeter of the upper generally tubular section 500, that is perpendicularly across the center axis of the handle housing 602.

A cap 620 is removably mounted to the bottom of the lower generally tubular section 502 to close the open bottom in the lower generally tubular section 502. As shown in FIGS. 33-36, the bottom of the lower generally tubular section 502 includes a cylindrical shape threaded region 624 and the cap 620 includes a round shape mating threaded region 626. The cap 620 is removably mounted to the bottom of the lower generally tubular section 502 by engagement between the round shape mating threaded region 626 of the cap 620 and the cylindrical shape threaded region 624 of the bottom of the lower generally tubular section 502.

As will be appreciated, the threaded connection of the detachable cap 620 allows for easy removal and installation of the cap 620 without any additional hardware, components, or tools such as fasteners or a screwdriver. With the cap 620 mounted to the handle housing 602, there is no exposed hardware and, consequently, cleanability is improved. Further, the removability of the cap 620 enables access to the downwardly opening bottom of the handle 600 and thus easy installation and/or replacement of the camera 604 or other components of the camera assembly 182 from the bottom of the handle housing 602 rather than for example removing the handle 600 from the light head housing 116, 122 and accessing the inside of the handle 600 through the top of the handle housing 602. The removability of the cap 620 also simplifies replacement of a camera glass 640 that forms part of the cap 620.

In the illustrated embodiment, the cylindrical shape threaded region 624 is an external thread and the round shape mating thread 626 is an internal thread. Of course, other types of threaded connections are possible and contemplated. For example, the cylindrical shape threaded region 624 may be an internal thread and the round shape mating thread 626 may be an external thread.

Referring now to FIGS. 37 and 38, the handle 600 includes a single printed circuit board (PCB) that is disposed in the handle housing 602. The handle 600 differs from the handle 164 of the FIGS. 3-6 embodiment in that the handle 600 has a single PCB disposed in the handle housing 602 whereas the handle 164 has two PCBs disposed in the handle housing 176. As described above, the PCB, or PCBs as the case may be, provides control electronics 305 for controlling the camera assembly 182 including the camera 184 in the FIGS. 3-6 embodiment or the camera 604 in the FIGS. 24-38 embodiment. As will be appreciated, the use of a single PCB instead of two or more PCBs reduces the volumetric footprint required by the PCB. The single PCB is disposed in the upper generally tubular section 500 of the handle housing 602, for example, within the inner perimeter of the upper generally tubular section 500. As shown in FIG. 38, the single PCB is relatively narrower in axial cross section than the width of the inner perimeter of the upper generally tubular section 500.

Although the invention has been shown and described with respect to certain preferred embodiments, it is understood that equivalents and modifications will occur to others skilled in the art upon the reading and understanding of the specification and the attached drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application. The present invention includes all such equivalents and modifications and is limited only by the scope of the following claims.

What is claimed is:

1. A surgical lighting system, comprising:
a light head housing including a plurality of light emitting elements therein that are arranged to emit light downward to a region of interest;
a handle mounted to the light head housing and protruding downward from the light head housing, the handle including a handle housing having a sufficient size to be gripped by the human hand;
a camera mounted within the handle housing, the camera having a field of view that encompasses at least a portion of the region of interest; and
an optical fiber cable that extends from a location within the handle housing and to the light head housing, the optical fiber cable being configured to transmit optical video signals associated with video data captured by the camera to the light head housing.

2. The surgical lighting system of claim 1, further comprising a fiber module within the handle housing and coupled to the optical fiber cable, wherein the fiber module is configured to convert electrical video signals of video data captured by the camera into the optical video signals.

3. The surgical lighting system of claim 2, further comprising a bracket that retains the fiber module in a fixed position relative to the camera.

4. The surgical lighting system of claim 3, wherein the bracket comprises a fiber module retention channel and the fiber module includes a flange that slidably fits into the fiber module retention channel.

5. The surgical lighting system of claim 3, wherein the bracket includes a retention wall that holds the fiber module against a camera assembly including the camera.

6. The surgical lighting system of claim 5, wherein the camera assembly includes a heat transfer plate in heat transmissive contact with the fiber module to draw heat away from the fiber module.

7. The surgical lighting system of claim 6, wherein the retention wall of the bracket holds the fiber module against the heat transfer plate.

8. The surgical lighting system of claim 6, further comprising a heat transfer pad sandwiched between the fiber module and the heat transfer plate, wherein the bracket compresses the heat transfer pad between the fiber module and the heat transfer plate.

9. The surgical lighting system of claim 5, wherein the bracket comprises an interface channel comprising a bottom wall and side walls, the interface channel extending between a proximal end and a distal end in a first direction, a distal wall located at the distal end of the interface channel and extending between the side walls, the distal wall comprising a slot providing fluid communication through the distal wall, the retention wall and fiber module retention channel located at the proximal end of the interface channel, the fiber module retention channel extending between a proximal end and a distal end in a second direction orthogonal to the first direction.

10. The surgical lighting system of claim 9, wherein a ferrule and a biasing member are coupled to the optical fiber cable at a distal end of the optical fiber cable, and the biasing member exerts a continuous force against the ferrule and the distal wall to position the distal end of the optical fiber cable against an optical video signal transmission port of the fiber module.

11. The surgical lighting system of claim 10, wherein the fiber module comprises a tubular interface member, and the ferrule is in contact with a distal end of the tubular interface member.

12. The surgical lighting system of claim 10, wherein a distal end of the optical fiber cable is laterally aligned with an axis of the optical video signal transmission port of the fiber module.

13. The surgical lighting system of claim 10, wherein a distal end of the optical fiber cable is angularly aligned with an axis of the optical video signal transmission port of the fiber module.

14. The surgical lighting system of claim 9, wherein the bracket further comprises a cable retention channel that guides the optical fiber cable within the handle housing.

15. The surgical lighting system of claim 14, wherein the interface channel and the cable retention channel extend parallel to one another.

16. The surgical lighting system of claim 14, wherein the cable retention channel comprises a linear portion and a curved portion having a predetermined radius of curvature.

17. The surgical lighting system of claim 14, wherein the optical fiber cable extends from the interface channel and is routed through the cable retention channel, and a portion of the optical fiber cable between the interface channel and the cable retention channel has a predetermined radius of curvature.

18. The surgical lighting system of claim 3, wherein a distal end of the optical fiber cable has a ferrule and the bracket includes an interface channel within which the ferrule seats to align the distal end of the optical fiber cable with an optical video signal transmission port of the fiber module.

19. The surgical lighting system of claim 18, wherein the bracket includes a biasing member that exerts a continuous force against the ferrule to compress the distal end of the optical fiber cable against the optical video signal transmission port of the fiber module.

20. The surgical lighting system of claim 19, wherein the interface channel has at its opposite ends a distal wall and the fiber module respectively, wherein the biasing member has a first end that exerts the continuous force against the ferrule and a second end that abuts the distal wall.

21. The surgical lighting system of claim 20, wherein the bracket includes a guide channel that guides the optical fiber cable within the handle housing and to the light head housing.

22. The surgical lighting system of claim 20, wherein the optical fiber cable has a bend radius as it passes between the distal wall and the light head housing.

23. The surgical lighting system of claim 3, wherein the bracket includes a receptacle that includes a first wall and a second wall opposite the first wall, wherein a ferrule and a biasing member are coupled to the optical fiber cable at a distal end of the optical fiber cable, and wherein the biasing member has a first end that exerts a continuous force against the ferrule and a second end that abuts the first wall.

24. The surgical lighting system of claim 2, wherein the fiber module is disposed between the camera and an inner perimeter of the handle housing.

25. The surgical lighting system of claim 1, wherein a portion of the optical fiber cable in the handle housing is bent at a predetermined radius of curvature.

26. The surgical lighting system of claim 1, wherein the camera is mounted within the handle housing for rotation within the handle housing about a rotation axis.

27. The surgical lighting system of claim 26, further comprising a fiber module within the handle housing and coupled to the optical fiber cable, wherein the fiber module is configured to convert electrical video signals of video data captured by the camera into the optical video signals, wherein the fiber module is disposed laterally to the side of and in spaced relationship relative the camera radially outward from the rotation axis of the camera.

28. The surgical lighting system of claim 1, wherein the light head housing is coupled to a distal end of an arm that is mounted for pivotable movement to a shaft.

\* \* \* \* \*